(12) United States Patent
Samakar et al.

(10) Patent No.: US 12,708,560 B2
(45) Date of Patent: Aug. 18, 2026

(54) IMPLANTABLE ELECTROMAGNETIC PUMPS

(71) Applicant: Verily Health Inc., Dallas, TX (US)

(72) Inventors: Amirhossein Samakar, South San Francisco, CA (US); Allister McGuire, South San Francisco, CA (US); Karthik Sekar, South San Francisco, CA (US); Dimitri Azar, South San Francisco, CA (US)

(73) Assignee: Verily Health Inc., Dallas, TX (US)

( * ) Notice: Subject to any disclaimer, the term of this patent is extended or adjusted under 35 U.S.C. 154(b) by 826 days.

(21) Appl. No.: 17/970,367

(22) Filed: Oct. 20, 2022

(65) Prior Publication Data

US 2023/0127855 A1 Apr. 27, 2023

Related U.S. Application Data

(60) Provisional application No. 63/270,398, filed on Oct. 21, 2021.

(51) Int. Cl.
*A61F 9/007* (2006.01)
*F04B 43/04* (2006.01)
(Continued)

(52) U.S. Cl.
CPC ........ *A61F 9/00781* (2013.01); *F04B 43/043* (2013.01); *H02K 3/04* (2013.01); *H02K 7/14* (2013.01)

(58) Field of Classification Search
CPC .. A61M 2205/0272; A61M 2205/3331; A61M 5/14224; A61M 5/14276; A61F 9/00781; F04B 19/006; F04B 43/043
See application file for complete search history.

(56) References Cited

U.S. PATENT DOCUMENTS 6,077,299 A 6/2000 Adelberg et al.
6,116,863 A * 9/2000 Ahn ........................ F04B 43/14 417/322

(Continued)

OTHER PUBLICATIONS

European Patent Office International Searching Authority, International Search Report and Written Opinion for PCT Application No. PCT/US2022/047334, International Filing Date Oct. 20, 2022; Search Report mailing date Apr. 11, 2023; 18 pages.

*Primary Examiner* — Kai H Weng
(74) *Attorney, Agent, or Firm* — Christensen O'Connor Johnson Kindness PLLC

(57) ABSTRACT

A micropump implantable in an eye is presented. In some aspects, the micropump includes a ferromagnetic member, a power source, and a motor coil magnetically coupled to the ferromagnetic member and electrically coupled to the power source to receive power from the power source. The motor coil is configured to generate a magnetic field in the ferromagnetic member when power is applied to the motor coil by the power source. In some embodiments, a hermetically sealed housing encloses the motor coil and the power source and partially encloses the ferromagnetic member. The micropump further includes a pump diaphragm and a compression chamber. The micropump further includes an armature configured to move in response to the magnetic field in the ferromagnetic member and a plunger configured to cause fluid to flow through the compression chamber from an inlet to an outlet.

15 Claims, 17 Drawing Sheets

(51) Int. Cl.

| | |
|---|---|
| ***H02K 3/04*** | (2006.01) |
| ***H02K 7/14*** | (2006.01) |

(56) References Cited

U.S. PATENT DOCUMENTS

| | | | |
|---|---|---|---|
| 6,168,575 | B1 | 1/2001 | Soltanpour |
| 6,589,198 | B1 | 7/2003 | Soltanpour et al. |
| 6,682,500 | B2 | 1/2004 | Soltanpour et al. |
| 8,915,893 | B2 | 12/2014 | Steinbach |
| 9,603,742 | B2 | 3/2017 | Sanchez et al. |
| 2005/0049578 | A1 | 3/2005 | Tu et al. |
| 2012/0191074 | A1 | 7/2012 | Steinbach |
| 2015/0257930 | A1 | 9/2015 | Lind |
| 2015/0335488 | A1 | 11/2015 | Bigler et al. |
| 2017/0348149 | A1 | 12/2017 | Stergiopulos et al. |
| 2019/0338230 | A1* | 11/2019 | Bhushan ................ C12M 21/08 |

* cited by examiner

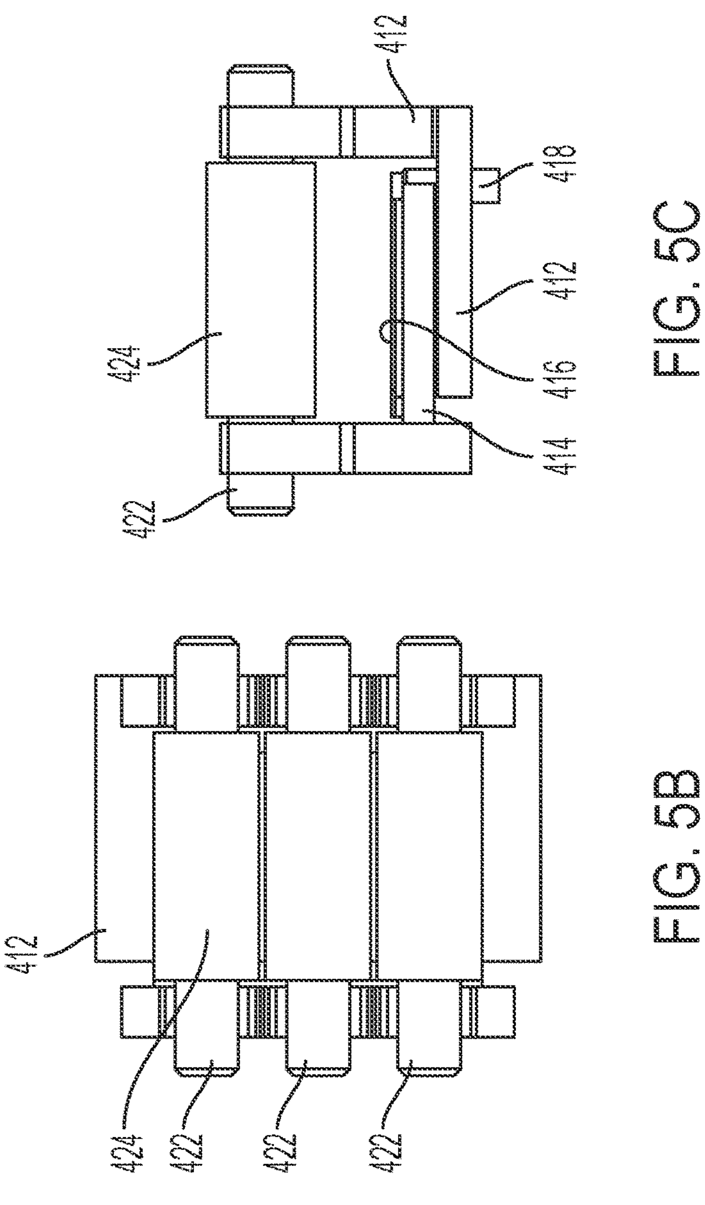
FIG. 5C
FIG. 5B
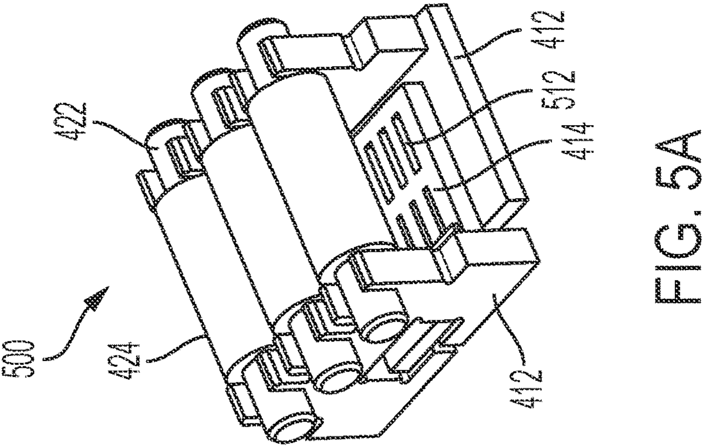
FIG. 5A 412
418
416
414

412
418
416
414
426

424
412
418
422
416
414
428
400
426

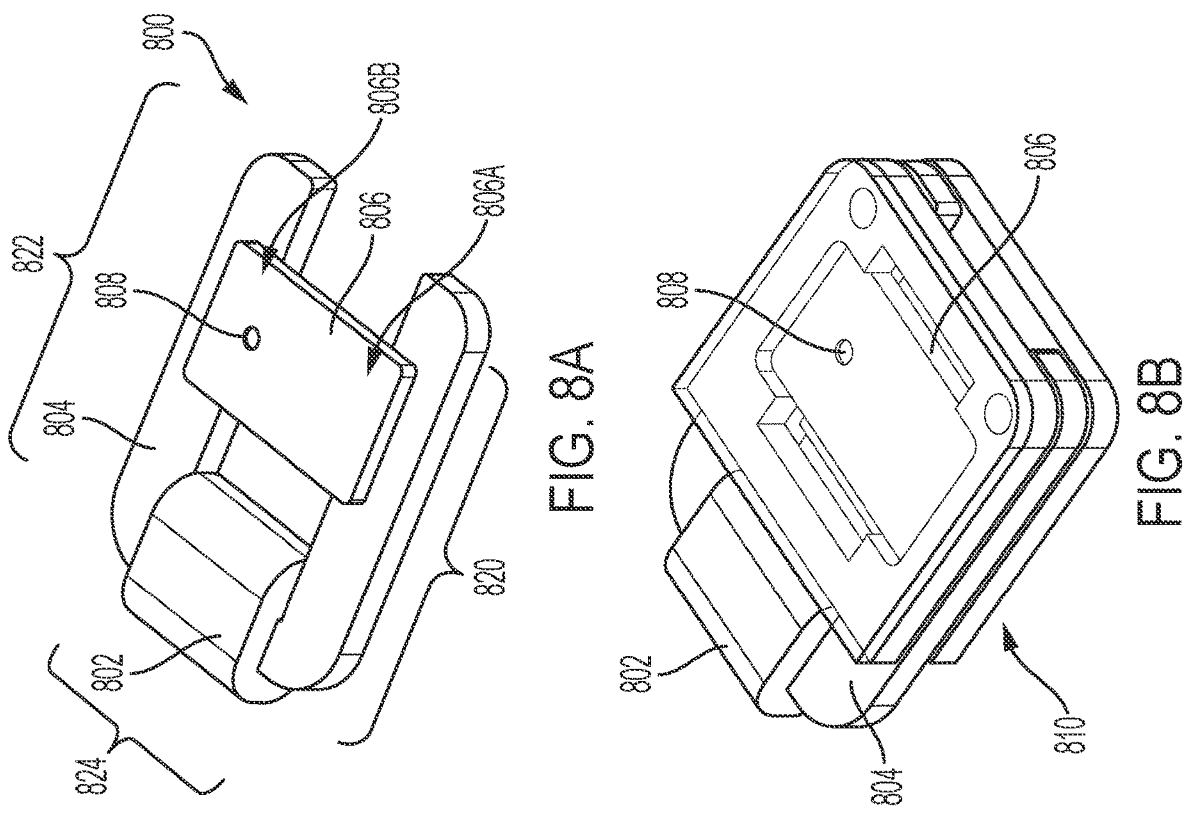
FIG. 8A
FIG. 8B
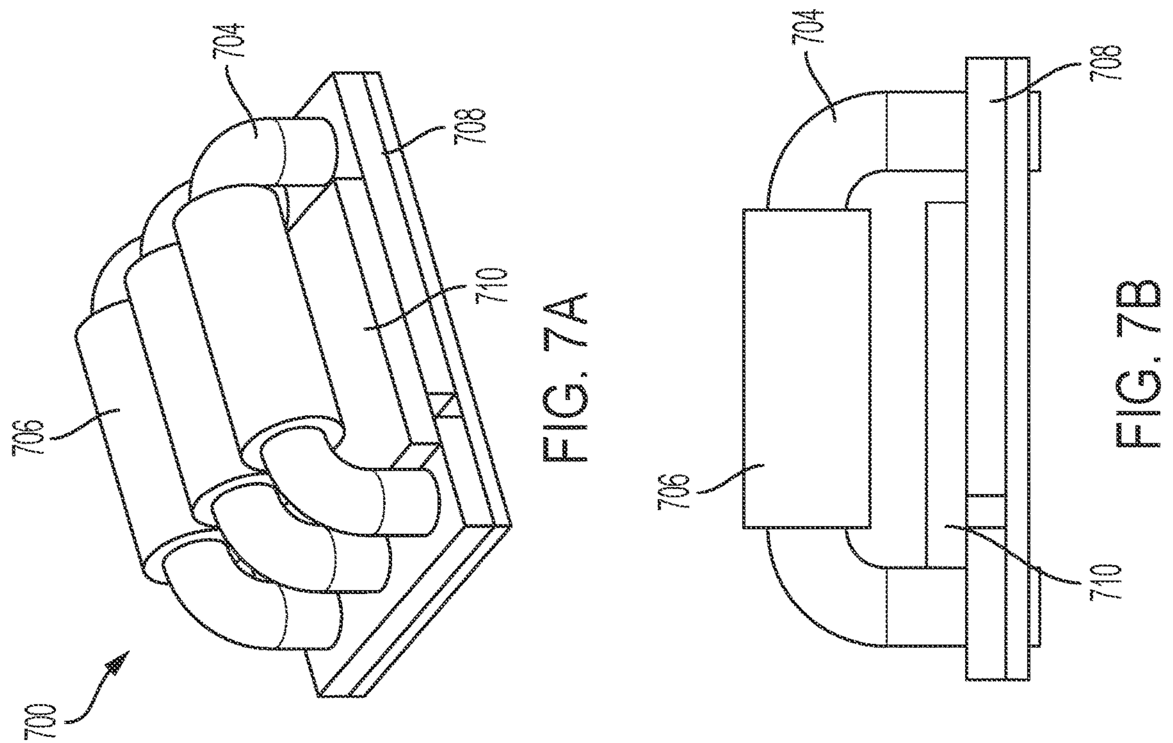
FIG. 7A
FIG. 7B

900

1004
1006
1002
1008

1006
1010
1002
1004
1000
1008

| Step | Inlet Valve | Pump | Outlet Valve | Inlet Flow | Outlet Flow |
|---|---|---|---|---|---|
| 1 | 0 | 0 | 1 | Y | N |
| 2 | 1 | 0 | 1 | N | N |
| 3 | 1 | 1 | 0 | N | Y |
| 4 | 0 | 1 | 1 | N | N |
| 5 (=1) | 0 | 0 | 1 | Y | N |

FIG. 16

| Step | Inlet Valve | Pump | Outlet Valve | Inlet Flow | Outlet Flow |
|---|---|---|---|---|---|
| 1 | 0 | 0 | 1 | Y | N |
| 2 | 1 | 0 | 1 | N | N |
| 3 | 1 | 0 | 0 | N | N |
| 4 | 1 | 1 | 0 | N | Y |
| 5 | 1 | 1 | 1 | N | N |
| 6 | 0 | 1 | 1 | N | N |
| 7 (=1) | 0 | 0 | 1 | Y | N |

FIG. 17

IMPLANTABLE ELECTROMAGNETIC PUMPS

CROSS-REFERENCE TO RELATED APPLICATIONS

The present application claims priority to, and the benefit of, U.S. Provisional Patent Application No. 63/270,398, filed Oct. 21, 2021, the entirety of which is incorporated by reference herein.

TECHNICAL FIELD

The present disclosure relates generally to implantable pumps and methods of using these pumps in fluid filled environments.

BACKGROUND

Miniature pumps, both implantable and externally placed, are used for a variety of medical purposes including injecting medicine into the body and withdrawing biofluids from the body. Some miniature pumps, also referred to as microfluidic pumps, are designed as membrane pumps that are activated by air pressure, but such pumps are not generally suitable for pumping biofluids in implantable devices. Other pump designs can place high stresses on diaphragms used within the pumps, but those diaphragms typically do not provide a hermetic seal for the electrical components, allowing water vapor to penetrate the pump causing damage and/or corrosion to the electronics. Furthermore, current microfluidic pumps have high energy consumption and/or require high pneumatic pressure. Thus, there is a need for a microfluidic pump that has a long operational life, a low energy consumption, and a small package size so that it can be implanted in the body.

SUMMARY

Implantable pumps and methods of using these pumps in fluid filled environments are described. In some aspects, a micropump implantable in the eye is presented. The micropump includes a ferromagnetic member, a power source, a motor coil, and a housing. The motor coil is magnetically coupled to the power source to receive power from the power source. The motor coil is configured to generate a magnetic field in the ferromagnetic member when power is applied to the motor coil by the power source. The housing encloses the motor coil and the power source and partially encloses the ferromagnetic member while being hermetically sealed. The micropump further includes a pump diaphragm, a compression chamber, an armature, and a plunger. The compression chamber is at least partially defined by the pump diaphragm and has an inlet and an outlet. The armature is configured to move in response to the magnetic field in the ferromagnetic member. The plunger is configured to actuate the pump diaphragm causing fluid to flow through the compression chamber from the inlet to the outlet in response to the movement of the armature. The pump diaphragm, the compression chamber, the armature, the plunger, and the portion of the ferromagnetic member are located outside of the hermetically sealed housing.

In some aspects, the present disclosure further describes an implantable micropump including a ferromagnetic core, a coil including multiple windings around the ferromagnetic core, and a ferromagnetic member connected to the ferromagnetic core. The micropump further includes a power source coupled to the coil and configured to provide power to the coil. The coil is configured to generate a magnetic field in the ferromagnetic core and the ferromagnetic member in response to the power supply providing power to the coil. The micropump further includes a housing that encloses the coil and the power source and partially encloses the ferromagnetic member. The housing is impervious, and a portion of the ferromagnetic member extends through the housing. The micropump further includes an armature that is configured to magnetically couple to the portion of the ferromagnetic member that extends through the housing. The armature is further configured to rotate in response to the magnetic field such that the rotation causes fluid to flow when the implantable micropump is immersed in fluid.

In some aspects, the present disclosure further describes an implantable device that includes a power source and a first ferromagnetic member having a first portion extending in a first direction, a second portion extending in the first direction, and a third portion extending in a second direction that is perpendicular to the first direction, wherein the third portion extends from the first portion to the second portion. The implantable device further includes a coil wrapped around the third portion that is electrically coupled to the power source. The coil is configured to generate a magnetic field in response to receiving power from the power source. The implantable device further includes a second ferromagnetic member positioned over the first portion and the second portion of the first ferromagnetic member such that the second ferromagnetic member is configured to move in response to the magnetic field. The movement causes fluid to flow from a first location to a second location. The implantable device further includes an enclosure surrounding the power source, the second ferromagnetic member and partially surrounding the first ferromagnetic member.

In some aspects, the present disclosure further includes a micropump implantable in an eye. The micropump includes a first motor having a first motor coil and a first plunger coupled to the first motor. The micropump further includes a second motor having a second motor coil and a second plunger coupled to the second motor. The micropump further includes a third motor having a third motor coil and a third plunger coupled to the third motor. The micropump further includes a power source coupled to the first motor coil, the second motor coil, and the third motor coil; and a housing enclosing the first motor coil, the second motor coil, the third motor coil and the power source, wherein the housing is hermetically sealed. In addition, the first plunger, the second plunger, and the third plunger are located outside of the housing. The micropump further includes a pump body located outside of the housing, the pump body including an inlet valve chamber, a compression chamber, and an outlet valve chamber. The first plunger is configured to selectively block and unblock the inlet valve chamber, the second plunger is configured to selectively block and unblock the compression chamber, and the third plunger is configured to selectively block and unblock the outlet valve chamber.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 5A-5C are perspective, top down, and side views of an exemplary three-core motor for use in an implantable micropump, according to various aspects of the present disclosure.

FIGS. 7A-7B are perspective and side views of an exemplary three-core motor for use in an implantable micropump, according to various aspects of the present disclosure.

FIGS. 8A-8B are perspective views of an exemplary motor for use in an implantable micropump, according to various aspects of the present disclosure.

FIGS. 10A-11B are perspective and side views of exemplary motors for use in an implantable micropump, according to various aspects of the present disclosure.

FIGS. 16 and 17 are tables of exemplary pump sequences, according to various aspects of the present disclosure.

DETAILED DESCRIPTION

Figure 1:
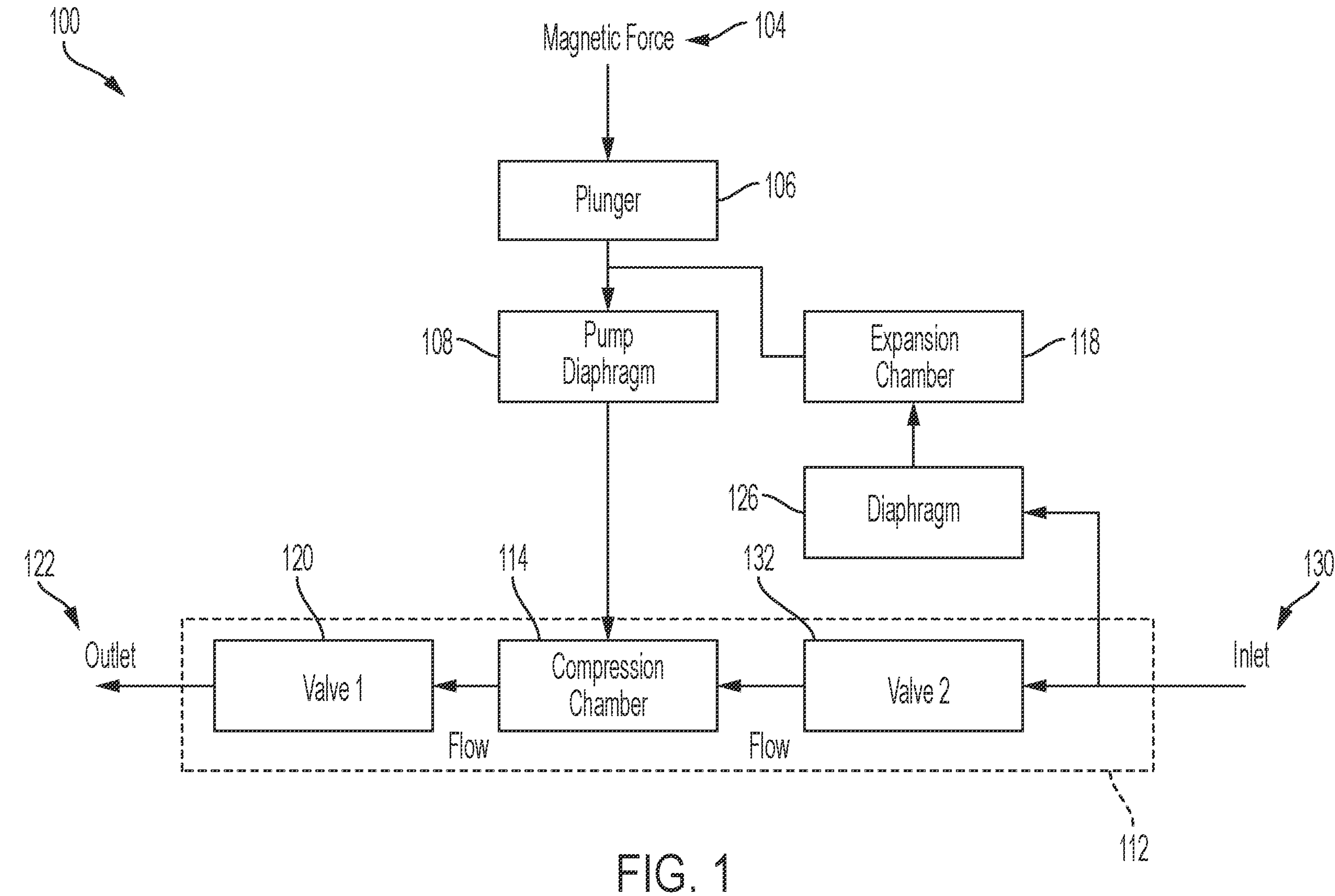
FIG. 1 is a functional system diagram of an exemplary implantable micropump, according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Disclosed herein are motors, also referred to as actuators, for operating miniature pumps immersed in fluids (e.g., microfluidic pumps) that can be implanted in the body. The devices and systems described herein may be used to inject medicine into the body and/or withdraw biofluids from the body. Disclosed herein are electric motors suitable for actuating the pumping mechanism of implantable microfluidic pumps. In some examples, the microfluidic pump may be implanted in the eye and used for regulating and controlling intraocular pressure (IOP). For example, devices presented herein may be surgically implanted or attached to a patient's eye to provide regulated drainage of aqueous humor out of the eye into a bleb in the conjunctiva of the eye or the tear film of the eye, which is an exterior surface of the eye.

Microfluidic pumps and motors discussed in the present disclosure include hermetically sealed, or impervious, enclosures for separating and protecting the electronics, including at least a portion of the electric motor, from the surrounding fluids, such as aqueous humor of the eye. The electric motor may be magnetically coupled to an actuator, or armature, that is configured to actuate a membrane in the microfluidic pump. In some embodiments, pressing and releasing the membrane causes fluid to flow through the pump.

Microfluidic pumps disclosed herein can have a long operational life with a low power consumption in a form factor suitable for implantation in a human eye. Devices discussed herein may have an operational life of about 10 years, with the diaphragms that are able to sustain over 300 million operations. Additionally, at least one embodiment has a low energy consumption being able to pump about 0.01 liter of fluid per joule of energy throughout the lifetime of the pump. A low energy consumption may be achieved by using at least one of the diaphragms disclosed herein, which requires only a small force to displace the diaphragm thereby causing fluid flow. As will be discussed further below, one way to achieve this is to integrate an armature of a magnetic motor into the pump body that is surrounded by fluid. Not only does this reduce power consumption but it also reduces size because certain moving parts are located outside of a hermetically sealed enclosure and immersed in a fluid.

Current electrostatic, magnetic, and piezo actuators are too large and/or require too high a voltage to be implanted. By contrast, actuators designed to be as small as 5×5×2 millimeters (mm), requiring only 3 volts (V) to operate, and having a stroke force of about 10 millinewtons (mN) for a 0.1 mm displacement are described further below. It is also desirable in some embodiments that such actuators are bistable (e.g., having two stable states) and simple to fabricate. Presented herein are actuators that employ a low power supply voltage and/or are compact, bistable, and/or simple to fabricate.

FIG. 1 is a functional block diagram of an implantable electromagnetic micropump 100, according to various embodiments of the present disclosure. FIG. 1 illustrates the relationship between various components of an implantable electromagnetic micropump 100. Implantable micropump 100 may include a plunger 106, a pump body 112, an expansion chamber 118, and a diaphragm 126 functionally interconnected as shown. The pump body 112 may include a compression chamber 114, a first valve 120, an outlet 122, an inlet 130, and a second valve 132 configured as shown. A volume generally existing for fluid flow between inlet 130 and outlet 122 may be referred to generally as a chamber or fluid chamber. A portion of the fluid chamber existing between the valves may be referred to as the compression chamber 114. The micropump 108 further includes a pump diaphragm 108. In some embodiments, the pump diaphragm 108 defines a portion of the compression chamber 114 and is considered a part of the pump body 112. For example, the inlet 130 may be configured for receiving aqueous humor from the eye, and the outlet 122 may be configured to discharge aqueous humor. In some embodiments, the outlet 122 is in fluid communication with an exterior surface of the eye so that aqueous humor is drained outside of the eye (e.g., onto the exterior surface).

A magnetic force 104 may be generated outside of the pump body 112. For example, the magnetic force 104 may be generated by a battery connected to an electric motor, and the electric motor may include a coil, or winding, of wires surrounding a ferromagnetic core, thereby forming an electromagnet. The magnetic force 104 may be sufficient to initiate movement of an armature (not shown) coupled to plunger 106, thereby moving plunger 106 into contact with pump diaphragm 108. Pressure created by the contact is sufficient to actuate, or engage, pump diaphragm 108.

Actuating pump diaphragm 108 can cause at least one action. In some embodiments, as a result of actuating pump diaphragm 108, a hydraulic pressure is created within compression chamber 114. The hydraulic pressure between pump diaphragm 108 and compression chamber 114 pushes the fluids that are in compression chamber 114 out of compression chamber 114 and through first valve 120. The fluid flows through the first valve 120 and out of the pump body 102 through an outlet 122.

In some embodiments, as a result of actuating pump diaphragm 108, a hydraulic pressure is created between pump diaphragm 108 and expansion chamber 118. The hydraulic pressure between pump diaphragm 108 and expansion chamber 118 creates another hydraulic pressure between expansion chamber 118 and diaphragm 126. Diaphragm 126 deforms into the expansion chamber 118 to compensate for pump diaphragm 108 deforming away from expansion chamber 118. Additionally, when diaphragm 126 deforms it creates a hydraulic pressure between diaphragm 126 and inlet 130 that draws fluid in through inlet 130. In some embodiments, diaphragm 126 may be a membrane through which fluid may flow. The flow of the fluid from inlet 130 into pump body 112, including into diaphragm 126, equalizes the change of volume on either side of diaphragm 126.

When magnetic force 104 is removed, plunger 106 moves away from pump diaphragm 108 allowing pump diaphragm 108 to return to its original position, thereby reducing the hydraulic pressure in compression chamber 114. First valve 120 prevents fluid from entering compression chamber 114 from outlet 122. Instead, fluid is pulled into compression chamber 114 through a second valve 132 from inlet 130, filling compression chamber 114. The hydraulic pressure between the pump diaphragm 108 and the expansion chamber 118 and the hydraulic pressure between expansion chamber 118 and diaphragm 126 are also removed, thereby returning diaphragm 126 to its original position. This sequence repeats as magnetic force 104 is applied to plunger 106 and removed from plunger 106 in order to pump fluid in from inlet 130, through pump body 112, and out outlet 122. The valves 120 and 132 may be check valves or other types of valves that perform the operations as discussed herein, such as plunger-actuated valves as described more fully herein below.

Figure 2:
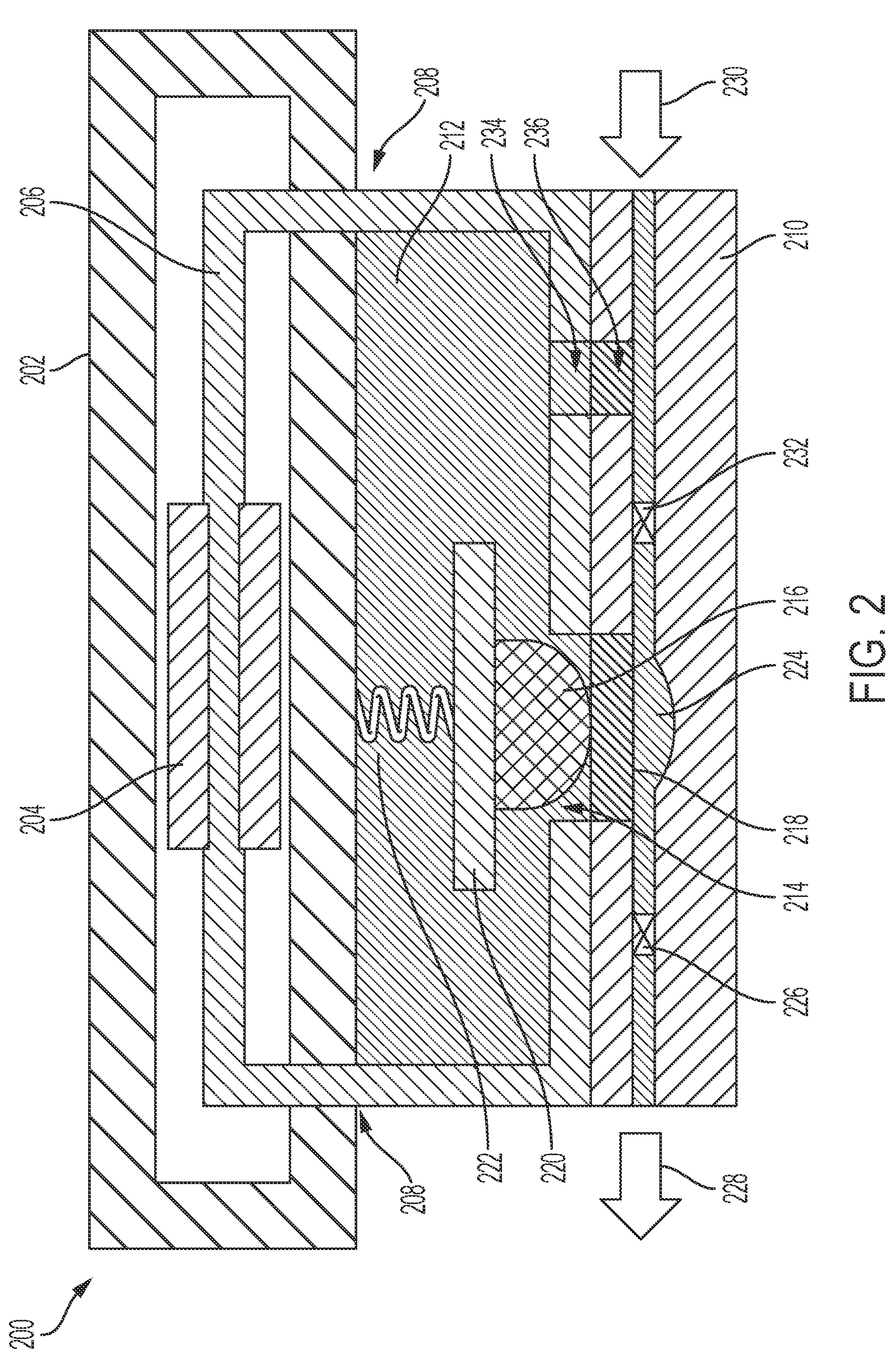
FIG. 2 is a cross section of an exemplary implantable micropump, according to various aspects of the present disclosure.

FIG. 2 is a cross section of a micropump 200, according to at least one embodiment of the present disclosure. In some embodiments, micropump 200 may be implanted in an eye to remove excess fluids from the eye, such as in the case of a glaucoma patient. Micropump design 200 includes an enclosure 202 that encloses all or a portion of a number of components of the micropump 200. The micropump 200 includes an electric motor used to operate a pumping mechanism. The electric motor of the micropump 200 includes a motor coil 204, a stator 208, and an armature 220 arranged as shown. In some embodiments, the motor coil 204 is a wire winding that is wrapped around the stator 206. A portion of the stator 206 resides within enclosure 202, and another portion of the stator resides outside of enclosure 202 as discussed further below. Enclosure 202 may further contain a battery, a capacitor, a microcontroller, an application specific integrated circuit (ASIC), and/or a sensor, such as a pressure sensor (not shown). When the micropump is immersed in a fluid, a pressure sensor may be used to measure the pressure of the fluid in which the enclosure 202 is immersed. In some embodiments, such as an application for reducing intraocular pressure, a processor, such as a microcontroller or an ASIC, receives pressure readings, such as intraocular pressure, from the sensor and determines when to activate the pump in order to pump fluid from the eye.

Enclosure 202 is hermetically sealed, or impervious, to protect the components contained inside from the fluids outside and may be filled with air and/or other gasses. Enclosure 202 may be constructed of ceramic and/or glass. Motor coil 204 may include a coil of wires surrounding a portion of stator 206 as shown. Stator 206 may be made from a ferromagnetic material such as iron, cobalt steel, electrical steel, or Permalloy 80. In some embodiments, motor coil 204 may be powered by the battery. In some other embodiments, motor coil 204 may be powered by the capacitor. In some embodiments, the capacitor may be a supercapacitor. The microcontroller, or ASIC, may determine when the motor coil 204 is powered on and powered off. Motor coil 204 generates a magnetic field when a power source, such as a battery or capacitor, applies a voltage to motor coil 204. The pump 200 is activated by the magnetic field generated by the motor coil 204. The magnetic field is conducted by stator 206 through the hermetically sealed enclosure 202 in order to activate the pump.

Enclosure 202 may include at least two feed-through points 208. Feed-through points 208 are openings in enclosure 202 that allow stator 206 to pass through enclosure 202 while maintaining the hermetic seal of enclosure 202. Generally, an O-ring or some type of sealant may be used to seal an opening such as feed through points 208. However, O-rings and other typical sealants may not provide long-lasting protection for an implanted micropump. As an alternative, feed through points 208 may be formed through a pour glass method that forms an air, and fluid, tight seal between enclosure 202 and stator 206 that ensures that enclosure 202 remains hermetically sealed.

The micropump 200 further includes a pump body 210. Stator 206 may be coupled to the pump body 210. The stator 206 may form a portion of an expansion chamber 212. For example, the volume of the expansion chamber 212 may be defined by a combination of surfaces of the stator 206, the enclosure 202, and the pump diaphragm 218 as shown. The expansion chamber 212 includes all or part of a plunger 216, an armature 220, and a spring 222. Expansion chamber 212 may be filled with water and/or another fluid as the parts inside of expansion chamber 212 are not sensitive to fluids. In some embodiments, expansion chamber 212 may be filled with air. Stator 206 includes an opening 214 through which plunger 216 may pass to contact pump diaphragm 218. As a nonlimiting example, plunger 216 may have a cylindrical shape, a spherical shape, or a rectangular shape. In some embodiments, plunger 216 has a radius between about 0.05 mm and about 0.5 mm, such as about 0.1 mm. In some embodiments, the end of the plunger 216 that contacts the pump diaphragm 218 is flat. In other embodiments, the end of the plunger 216 that contacts the pump diaphragm 218 (also referred to as diaphragm 218) is rounded, or spherical. The spherical radius of the end of plunger 216 may be between about 0.5 mm and about 1.5 mm, such as about 1.2 mm. Through experimentation, a plunger 216 that provides desirable performance was determined to have a cylindrical shape with a radius of about 0.1 mm and a flat end contacting pump diaphragm 218.

In some embodiments, diaphragm 218 may be made from thermoplastic elastomers (TPE) or silicone. At least two competing concepts may be balanced in determining the diameter of diaphragm 218. First, as the diameter of a diaphragm increases the stiffness of the diaphragm decreases. That is, the amount of force required to deform, or move, the diaphragm decreases. Second, as the diameter of a diaphragm increases the area of the diaphragm increases. This increase in area increases the force necessary to overcome back pressure. In other words, the force necessary to move the fluid. Analysis has determined that a diameter of between about 0.75 mm and about 2 mm is suitable for micropump 200. In some embodiments, a diameter of about 1 mm provides desirable performance. Diaphragm 218 may have a thickness of between about 0.05 mm and about 0.2 mm. In some embodiments, plunger 216 may be displaced axially about 0.1 mm or more, thereby causing diaphragm 218 to deform, or stretch, about 0.1 mm or more at a point of contact with plunger 216.

Plunger 216 is connected to the armature 220. Armature 220 may be rectangular shaped having plunger 216 connected to one side and spring 222 connected to an opposing side. In some embodiments, armature 220 consists mainly or solely of ferromagnetic material, such that it is attracted by a magnetic field. When a voltage is applied to motor coil 204 a magnetic field is induced in stator 206. Voltage may be applied to motor coil 204 using an electric power source, such as a battery or a capacitor, located in the enclosure 202. The magnetic field induced in stator 206 attracts armature 216 causing armature 220 to move toward the pump diaphragm 218. The movement of armature 220 axially displaces plunger 216 causing it to engage, or actuate, pump diaphragm 218. Actuating pump diaphragm 218 may include moving, or displacing, pump diaphragm 218 into compression chamber 224. In some embodiments, armature 220 may be larger than opening 214 so that armature 220 does not pass through opening 214 but contacts stator 206. In other embodiments, after the armature 220 is displaced in a direction toward the stator 206, the tension of spring 222 in an opposing direction counterbalances the force of attraction in the other direction caused by a magnetic field in the stator 206 attracting armature 220, such that armature 220 comes to a stop after a certain displacement. When the magnetic field is removed from stator 206, spring 222 pulls armature 220 in a direction opposite the pump diaphragm

218. This disengages plunger 216 from pump diaphragm 218, allowing pump diaphragm 218 to return to its original position.

The magnetic field is generated in stator 206 as motor coil 204 is powered on and powered off in a cycle. When the magnetic field is present in stator 206, armature 220 is drawn toward diaphragm 218 thereby engaging plunger 216 to deform pump diaphragm 218. When the magnetic field is removed, spring 222 pulls armature 220 away from stator 206, disengaging plunger 216 from pump diaphragm 218. The movement of pump diaphragm 218 into compression chamber 224 pushes fluid through a first check valve 226 and out an outlet 228. The movement of pump diaphragm 218 out of compression chamber 224 pulls fluid from an inlet 230 and through a second check valve 232 in compression chamber 224. First check valve 226 is designed to allow fluid to flow from compression chamber 224 to outlet 228 but prevent fluid from flowing the opposite direction. Similarly, second check valve 232 is designed to allow fluid to flow from inlet 230 and into compression chamber 224 but prevent fluid from flowing the opposite direction. In this manner fluid is pumped from inlet 130 through the micropump 200 and out outlet 228. In some embodiments, pump 200 may not include first check valve 226 and second check valve 232. Also, in some embodiments, check valves 226 and 232 may instead be implemented as valves other than check valves. For example, the check valves 226 and 232 may instead be plunger-actuated valves, as discussed below herein, or other types of valves.

As pump diaphragm 218 moves it changes the pressure in compression chamber 224 and it also changes the pressure in expansion chamber 212. In at least one embodiment, to maintain a relatively constant pressure in expansion chamber 212 a hole 234 is provided in stator 206 and an opening 236 is provided in pump body 210. The hole 234 and opening 236 are at least partially aligned so that fluid is allowed to flow into and out of the expansion chamber 212.

In some embodiments, opening 236 allows fluid to flow between inlet 230 and expansion chamber 212 through hole 234. When motor coil 204 is powered on, fluid flows through opening 236 into expansion chamber 212 as plunger 216 engages pump diaphragm 218 to push fluid from compression chamber 224 out of pump body 210. While opening 236 is the simplest solution, problems may arise when the fluid being pumped contains particles. Particles inside expansion chamber 212 can interfere with spring 222, armature 220, and/or plunger 218.

In some embodiments, opening 236 is covered by a membrane (not shown) having small pores to filter the fluid. The membrane may act as a filter with the small pores (e.g., 1 μm pore size) filtering any particles from the fluid as it flows from inlet 230 into expansion chamber 212. With the membrane in opening 236 the pump functions the same as with just the opening 236. The membrane protects the components inside expansion chamber 212 from the particles in the fluid.

In some other embodiments, opening 236 may include a diaphragm, an elastic membrane, a bellow, or a balloon structure. The diaphragm in opening 236 will expand and contract (or deform and reform) into the expansion chamber 212 as pump diaphragm 218 is pushed into and out of compression chamber 224. The diaphragm 236 will restrict any particles in the fluid from entering the expansion chamber 212. Such an embodiment may be beneficial when expansion chamber 212 is filled with air.

In some embodiments, the micropump 200 is implanted in a human eye. The inlet 230 may be configured for receiving aqueous humor from the eye, and the outlet 228 may be configured to discharge aqueous humor. In some embodiments, the outlet 228 is in fluid communication with an exterior surface of the eye so that aqueous humor is drained outside of the eye (e.g., onto the exterior surface).

Figure 3B:
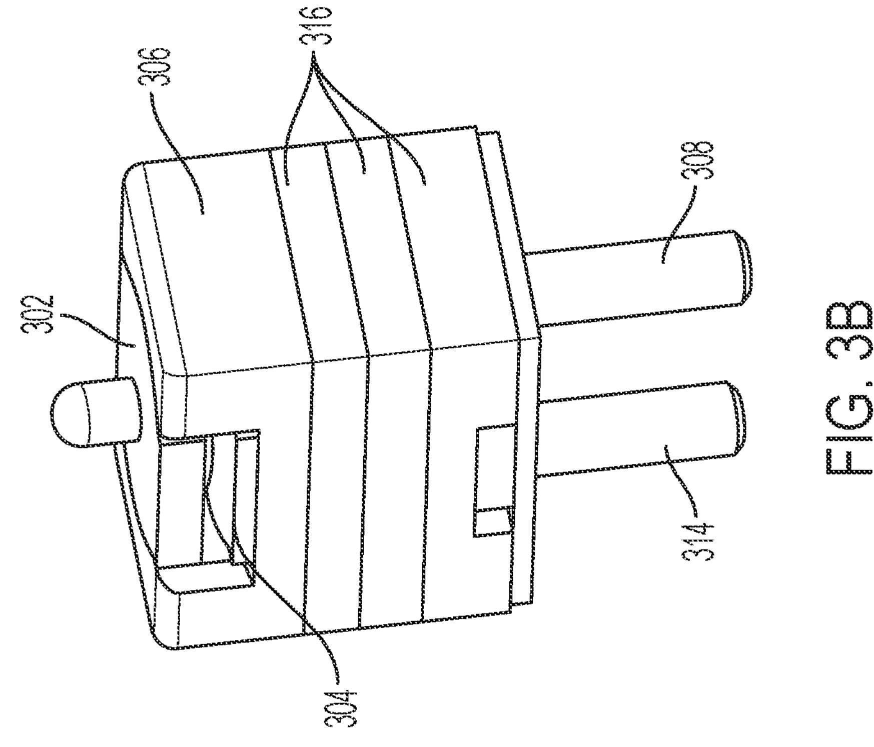
FIGS. 3A-3C are side, perspective, and exploded illustrations of an exemplary pump body for use with an implantable micropump, according to various aspects of the present disclosure.
Figure 3A:
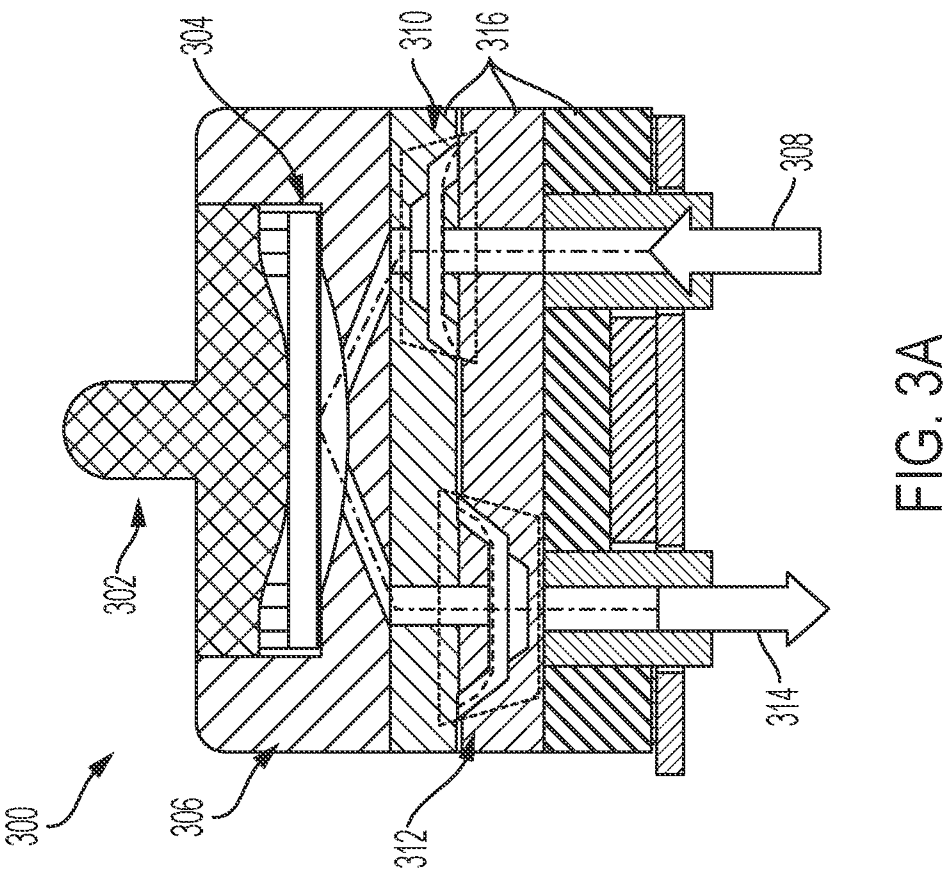
Figure 3C:
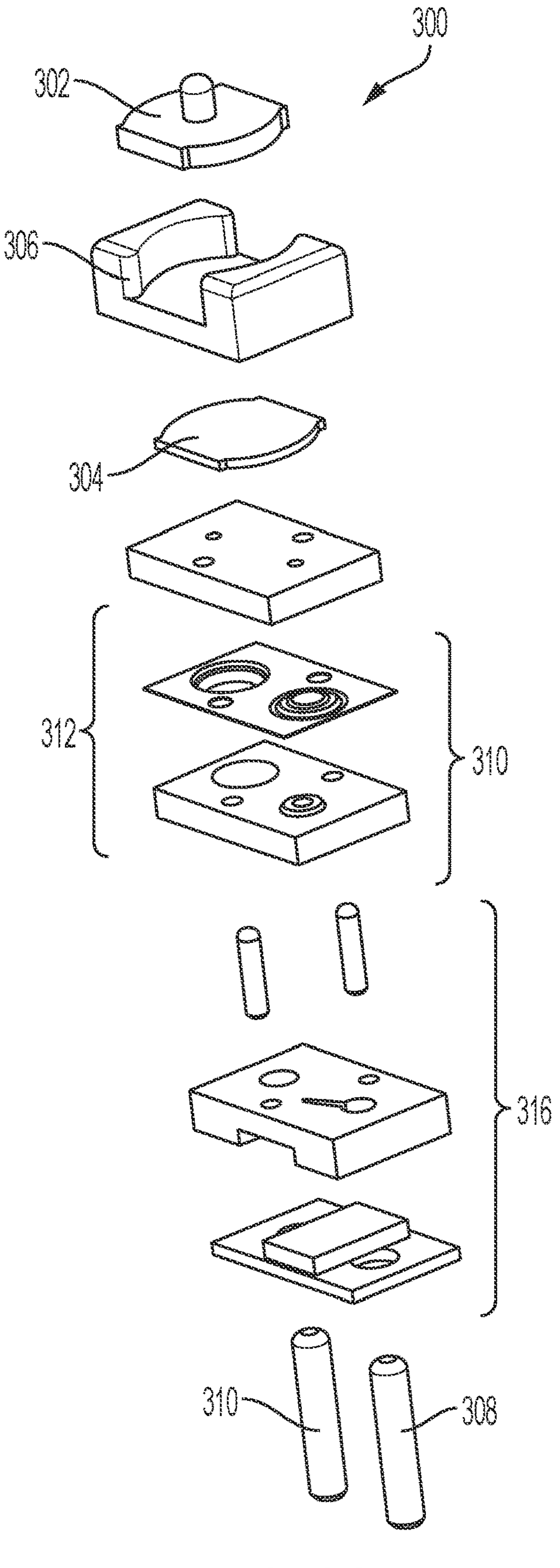

Turning to FIGS. 3A-3C, illustrated are side, perspective, and exploded views of an exemplary pump body 300 according to embodiments of the present disclosure. Pump body 300 follows the principles discussed above with respect to electromagnetic pump 100. Pump body design 300 may be an example of pump body 210 discussed above with respect to micropump design 200. Pump body 300 includes a plunger 302, a diaphragm 304, a compression chamber 306, an inlet 308, an inlet check valve 310, an outlet check valve 312, an outlet 314, and additional support structures 316 to contain all of the components.

When activated, plunger 302 engages diaphragm 304, pushing diaphragm 304 into compression chamber 306. In the depicted embodiment, plunger 302 is sized and shaped to fit into and fill compression chamber 306 as it engages, or actuates, diaphragm 304. In some other embodiments, plunger 302 may be a cylinder with a flat or rounded end for engaging diaphragm 304.

Diaphragm 304 may be made of a soft biocompatible elastomer such as silicone or thermoplastic elastomer. Such soft biocompatible elastomer materials have viscoelastic properties and high fatigue limits compared to the operating stress. These properties allow the diaphragm 304 to stretch, or deform, when stress is applied (e.g., by plunger 302) and to return to its original shape when the stress is removed. The high fatigue limit allows diaphragm 304 to be stretched and deformed millions of times over the life of the product.

Inlet check valve 310 and outlet check valve 312 may be exemplary embodiments of second check valve 232 and first check valve 226, respectively, discussed above with respect to FIG. 2. Inlet check valve 310 allows fluid to flow from inlet 308 into compression chamber 306 but prevents flow in the reverse direction. Outlet check valve 312 allows fluid to flow from compression chamber 306 to outlet 314 but prevents flow in the reverse direction. When connected to a motive force, pump body 300 pumps fluids from inlet 308 to outlet 314.

Components of pump body 300 (e.g., compression chamber 306, support structures 316, etc.) are protected against biofouling. In some embodiments, pump body 300 may be coated in an antifouling coating such as PEG. In some embodiments, pump body 300 may have surface textures applied to surfaces that may come in contact with biofluids. In some embodiments, hydrophilic coatings may be applied to surfaces that come in contact with biofluids. In some embodiments, one or more of antifouling coating, surface texture, and/or hydrophilic coatings may be applied in combination to protect pump body 300 from biofluids.

Figure 4:
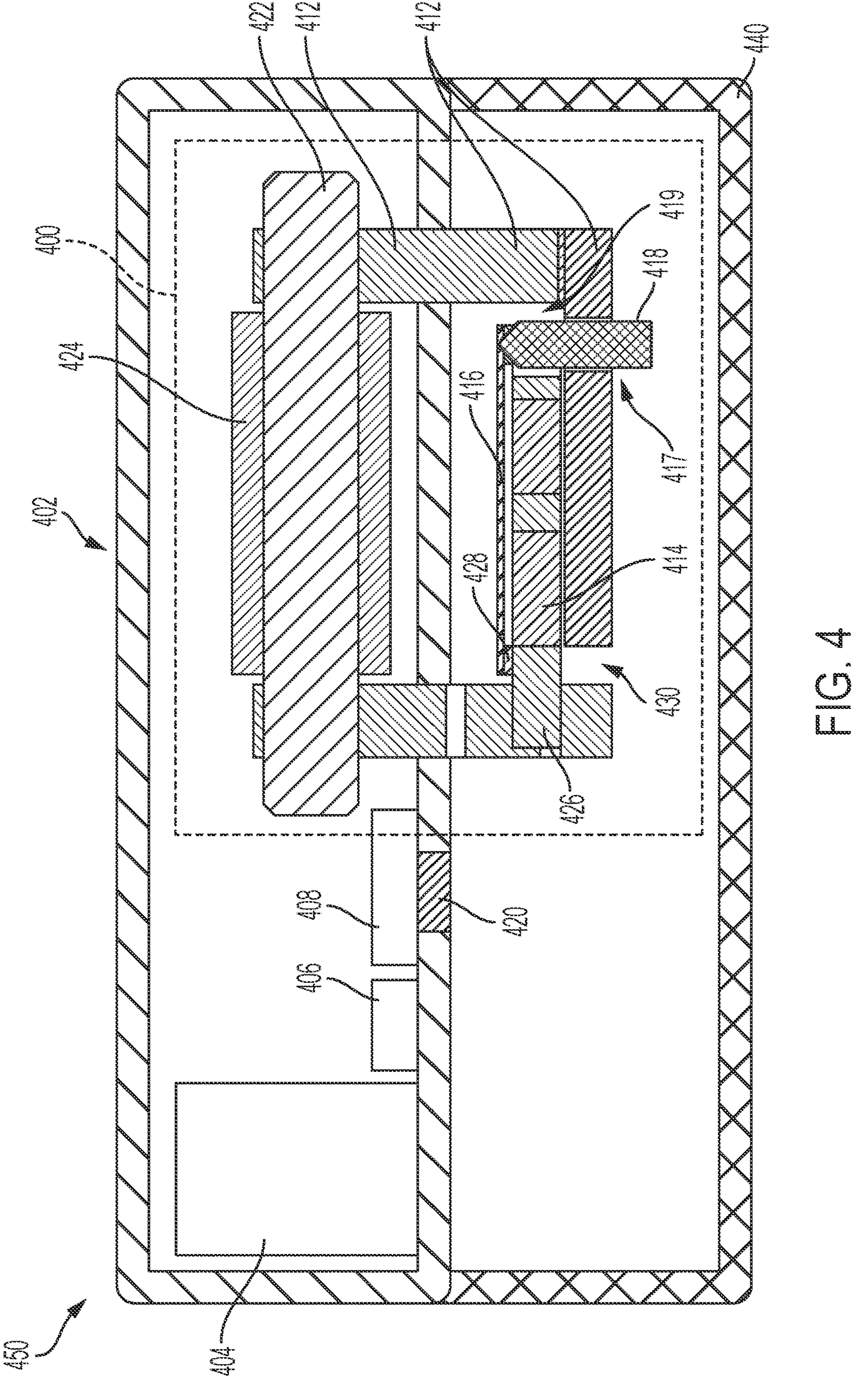
FIG. 4 is a cross section of an exemplary motor assembly for use in an implantable micropump, according to various aspects of the present disclosure.

Turning to FIG. 4, illustrated is an exemplary motor assembly 450, according to various embodiments of the present disclosure. Motor assembly 450 may be coupled to pump body 300 and be configured to actuate pump body 300 such as by moving, or displacing, plunger 302. Motor assembly 450 includes an enclosure 402 including a power source 404 (e.g., battery or capacitor), an integrated circuit (IC) 406, a sensor 408, and an electric motor 400 as shown. The electric motor 400 includes a motor core 422, a motor coil 424, and a first portion of stator 412, all located inside of enclosure 402. Outside of enclosure 402, motor 400 further includes a second portion of stator 412, an armature 414, a spring 416, and a plunger 418 as shown. Motor assembly 450 may also optionally include an enclosure 440 that at least partially encloses the components outside of enclosure 402 as shown.

Motor assembly 450 may be implanted and/or immersed in fluids. Enclosure 402 is an air and/or gas filled enclosure that is hermetically sealed, or impervious, to ensure that no fluids enter enclosure 402. Outside of enclosure 402 is a fluid filled environment. Stator 412 extends from inside enclosure 402 through walls of enclosure 402 to outside of enclosure 402. The electronic components of motor assembly 450 (e.g., power source 404, IC 406, sensor 408, motor core 422 and motor coil 424) are placed inside of enclosure 402 and are protected from the fluid outside of the enclosure 402. In some embodiments, enclosure 402 may be filled with a plastic, further protecting the electronic components inside.

The enclosure 440 is open to allow fluids in the eye to enter the enclosure 440 in the fluid filled environment.

Power source 404 may provide power at least to IC 406, sensor 408, and motor coil 424. Motor coil 424, IC 406, and sensor 408 may use a low voltage power supply. Accordingly, power source 404 may be a low voltage battery between about 3 V and about 4.5 V. In some other embodiments, power source 404 may be a capacitor providing voltage to the motor coil 424, IC 406, and sensor. The capacitor may be recharged using an external power supply. The voltage from power source 404 may be provided directly to motor coils 424. In some embodiments, the voltage from the power source 404 may pass through IC 406 before being provided to motor 410.

IC 406 may be a microcontroller or an application specific integrated circuit (ASIC) or other sort of processor. IC 406 may control the motor coil 424 and sensor 408. Sensor 408 may be a pressure sensor that detects the pressure of the fluid surrounding enclosure 402 through an opening 420 in enclosure 402. IC 406 may receive pressure readings from sensor 408 and control motor coil 424 accordingly. In some examples, that may mean operating motor 400 at a higher frequency when the sensor 408 reads a high pressure. In some other examples, that may mean operating motor 400 at a lower frequency when the sensor 408 reads a high pressure. In either example, IC 406 controls motor coil 424, and motor 400 by extension, in response to readings from sensor 408. In some embodiments, motor assembly 450 does not have a sensor 408 and IC 406 controls motor coil 424 according to a pre-programmed cycle.

Motor coil 424 may be a conductive winding, such as a wire, around motor core 422. While FIG. 4 depicts a cross section of a single motor core 422 and coil 424, motor 400 may include one or more motor cores 422 and motor coils 424, such as illustrated in FIG. 5. Motor core 422 may be made of ferromagnetic metal or alloys such as, for example, electrical steel, metglas, cobalt steel, nickel steels, stainless steels, low carbon steels, electrical iron, or Permalloy 80. Motor coil 424 may be made of copper wire. When an electrical current is passed through motor coil 424 a magnetic field is created that induces an electric current in motor core 422. Motor core 422 is electrically coupled to stator 412. The electric current in motor core 422 passes through stator 412 and creates a magnetic field around stator 412. The strength of the electric current and associated magnetic field is determined in part by the size and number of windings in motor coil 424. The magnetic torque of motor 400 increases as the length of motor coil 424 increases. The magnetic torque of motor 400 decreases as the wire radius of motor coil 424 and the radius of motor core 422 decrease.

Accordingly, the diameter of the wire used in motor coil 424 may be between about 10 μm and about 35 μm.

Stator 412 includes an attachment point 426, an opening 417 and an opening 430. Armature 414 includes a first end and an opposing second end where the first end of armature 414 is coupled to stator 412 at attachment point 426 so that armature 414 rotates about attachment point 426. The first end of armature 414, close to attachment point 426, includes an attachment point 428 and the second end of armature 414 includes an opening 419. Spring 416 is coupled to armature 414 at attachment point 428, close to the first end of armature 414. Plunger 418 passes through opening 419 in armature 414 and opening 417 in stator 412 with little to no contact with armature 414 and stator 412. Plunger 418 has a first end and an opposing second end. Spring 416 contacts the first end of plunger 418 and is configured to move plunger 418 in an axial direction through openings 417, 419. The second end of plunger 418 may be configured to engage, or actuate, a pump diaphragm (not shown in FIG. 4), such as for example diaphragm 304 of pump body 300. Opening 430 may allow fluid to flow around, or through, stator 412 which may equalize fluid pressure as armature 414 and spring 416 move. A pump diaphragm may be located in or on enclosure 440.

Turning to FIGS. 5A-5C, illustrated are perspective, top, and side views, respectively, of an exemplary three-core motor 500 that is similar to the single core motor 400 described above. Three-core motor 500 includes three cores 422 and three motor coils 424 and armature 414 includes at least one slot 512. Three-core motor 500 functions similarly to motor 400 with addition of each motor core 422 being electrically coupled to stator 412. Including three motor cores 422, and motor coils 424, may provide three-core motor 500 with more power than motor 400, having a single core. The at least one slot 512 may serve to decrease the drag of armature 414 as it moves through the fluid, as described above with respect to FIG. 4 and will be further described below.

Figures 6A, 6B, 6C:
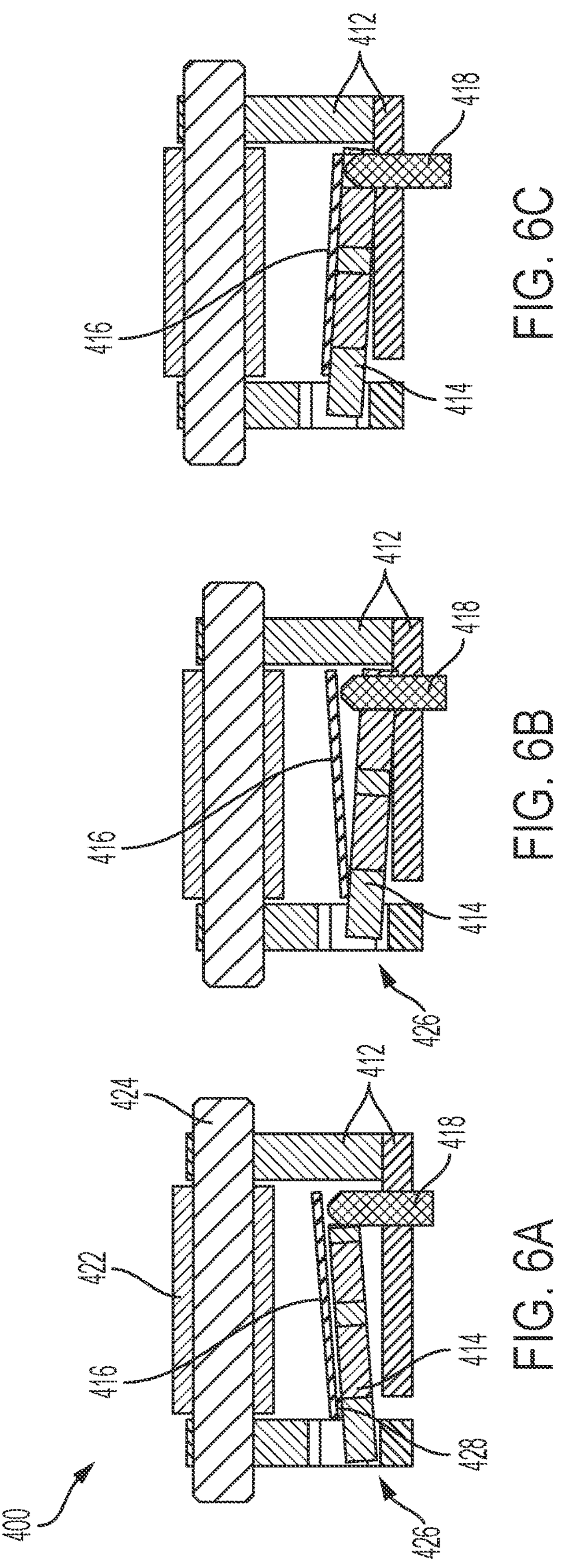
FIGS. 6A-6C are cross section views of the operation of an exemplary motor for use in an implantable micropump, according to various aspects of the present disclosure.

Turning to FIGS. 6A-6C, illustrated are three states of operation of motor 400 and/or three-core motor 500. For simplicity and clarity all the discussion below will refer to motor 400 while the same applies to three-core motor 500 as well. FIG. 6A depicts a powered off, or initial, state, FIG. 6B depicts a powered on, or high power, state, and FIG. 6C depicts a powered on steady, or locked, state. In FIG. 6A, motor 400 is in the initial state with motor 400 powered off. A first end of plunger 418 is contacting spring 416 and a second opposing end of plunger 418 may be contacting a diaphragm, or other movable structure. In the initial state, the force of the diaphragm, or other movable structure, pushing on plunger 418 provides sufficient tension to move spring 416 in a direction away from stator 412 and hold spring 416 there. The tension in spring 416, caused by plunger 418, moves armature 414 away from stator 412 and holds armature 414 there. Spring 416 is considered pre-loaded in the powered off state.

At a moment between FIGS. 6A and 6B, a voltage is applied to motor coil 424 and motor 400 becomes powered on and enters a high-power state. Voltage may be applied to motor coil 424 from power source 404 (e.g., battery or capacitor). In some embodiments, voltage from power source 404 may be applied directly to motor coil 424. In some other embodiments, voltage from power source 404 may pass through IC 406 before being applied to motor coil 424. IC 406 may control, or regulate, how the voltage is applied to motor 400. When motor 400 is powered on, such as in the high-power state, a magnetic field may be induced in stator 412 and create an electric current in stator 412. The magnetic field attracts armature 414 to stator 412 causing armature 414 to begin to move. The force required to move armature 414 is inversely proportional to the size of the gap between armature 414 and stator 412. That is, a larger gap between armature 414 and stator 412 requires less force to move armature 414. In some embodiments, the gap between armature 414 and stator 412 may be between about 85 μm and about 100 μm. Additionally, the amount of motive force provided by the magnetic field is proportional to the square of the current in stator 412. For example, in order to increase the amount of force two-fold the current in stator 412 must be increased four-fold. Therefore, in order to conserve energy, IC 406 may provide as small a voltage, or current, as possible to motor coil 424 while stator 412 still maintains sufficient force to move plunger 418. In some embodiments, the current may be between about 0.8 mA and about 1.2 mA.

Turning to FIG. 6B, armature 414 has rotated in response to the magnetic field of stator 412 and is now in contact with stator 412. Armature 414 rotates about point 426 and may rotate between about 5° and about 15° from start to finish (e.g., contacting stator 412) such as about 10°. In some embodiments, armature 414 may include at least one hole and/or slot to decrease drag caused by the surrounding fluid. While armature 412 responds quickly to the magnetic field of stator 412, spring 416 is comparatively slower to respond. Motor 400 may enter a low power, or locked, state while keeping armature 414 in contact with stator 412 giving sufficient time for spring 416 to respond to the movement of armature 414. As spring 416 responds to the movement of armature 414, it pivots about point 428, pushing plunger 418 in an axial direction, in order to return to its original, preloaded, state and position against armature 414.

Turning to FIG. 6C, spring 416 has axially translated plunger 418 to an end point and has returned to its preloaded state. Motor 400 may still be in a low power state and still generating a magnetic field to maintain armature 414 in contact with stator 412 which maintains spring 416 in contact with armature 414. In the lower power state, spring 416 maintains pressure on plunger 418 keeping plunger 418 in depressed, or pushed into a diaphragm, such as for example pump diaphragm 218 describe above with respect to FIG. 2 or diaphragm 304 described above with respect to FIG. 3. In some embodiments, there is no air gap between armature 414 and stator 412 in the locked state. In some other embodiments, plunger 418 maintains sufficient tension on spring 416 to stop armature 414 after a certain displacement and before contacting stator 412.

Motor 400 is then powered off, that is the voltage is no longer applied to motor coil 424. Motor coil 424 no longer induces a magnetic field in stator 412 and stator no longer attracts armature 414. Pin 418 may be axially translated in the opposite direction as before by the diaphragm, or other structure, which provides tension in spring 416. The tension in spring 416 moves spring 416 in the opposite direction of the plunger 418 and stator 412. As spring 416 moves away from stator 412, spring 416 causes armature 414 to rotate away from stator 412 because they are coupled at attachment point 428. Motor 400 returns to its original position, as depicted in FIG. 6A.

Turning to FIGS. 7A-7B, illustrated are perspective and side views of a motor 700 according to at least one embodiment of the present disclosure. Motor 700 includes three motor cores 704, three motor coils 706, a stator 708, and an armature 710. Each motor core 704 is formed into a shape as illustrated having two ends with each of the ends of motor core 704 inserted into stator 708. Stator 708 may be constructed from six different pieces and be configured to receive each of the motor cores 704 and support armature 710. Armature 710 contacts stator 708 but is not connected to stator 708. Stator 708 includes an opening through which a pin, or a plunger, may pass with little to no contact with stator 708. The mechanics of motor 700, including armature 710, will be described in more detail with respect to FIG. 8 as each embodiment functions similarly.

Turning to FIGS. 8A-8B, illustrated are perspective views of a device 800 according to at least one embodiment of the present disclosure. Device 800 includes a motor coil 802, a stator 804, an armature 806, and an enclosure 810. Stator 804 may be constructed from iron or Permalloy 80, as just a few examples. Stator 804 may be fabricated from a single piece of ferromagnetic material, such as a metal or alloy. Stator 804 may be integrally formed having a first portion 820 extending in a first direction, a second portion 822 extending in the first direction and substantially parallel to the first portion, and a third portion 824 extending from the first portion 820 to the second portion 822 in a second direction. The second direction may be perpendicular to the first direction. The first portion 820 has a first end and an opposing second end, the second portion 822 has a first end and an opposing second end, and the third portion 824 extends from the first end of the first portion 820 to the first end of the second portion 822. Motor coil 802 may be wrapped around a portion of the stator 804, such as the third portion 824. In some embodiments, motor coil 802 may include wire wrappings around the third portion of stator 804 that extend from the first end of the first portion of stator 804 to the first end of the second portion of stator 804. This makes device 800 easy to manufacture and assemble as stator 804 also functions as a motor core around which motor coils 802 are wrapped.

Enclosure 810 may surround, or enclose, armature 806 and the second end of the first portion of stator 804 and the second end of the second portion of stator 804. Armature 806 is disposed above stator 804, within enclosure 810, and may physically contact stator 804 but armature 806 is not connected, or attached, to stator 804. Armature 806 may be fabricated from a single piece of ferromagnetic material, such as a metal or alloy. While enclosure 810 constrains the movement of armature 806, armature 806 maintains some freedom of movement so that it is not always contacting stator 804. Armature 806 includes a first end 806A disposed over the first portion of stator 804, an opposing second end 806B disposed over the second portion of stator 804, and a recess 808 for receiving a plunger near the second end 806B. In some examples, the plunger may be plunger 418 as discussed above with respect to FIG. 4. Armature 806 may be between about 150 μm and 250 μm thick. In some embodiments, armature 806 may be about 200 μm thick. In some embodiments, armature 806 includes multiple square shaped holes to reduce the drag of armature 806 as it moves through the fluid. Each hole may be about 0.1 mm×0.1 mm in size.

In some embodiments, a second enclosure (not shown) may surround motor coil 802 and a portion of stator 804 (e.g., the third portion 824 of stator 804). The enclosure may include a power source and an integrated circuit (IC) for controlling device 800 by providing power (e.g., applying a voltage) to motor coil 802. Examples of such a power source and integrated circuit are illustrated in FIG. 4. The second enclosure may be hermetically sealed to prevent fluid from entering the enclosure. In some embodiments, a flowed glass process may be used to seal portions of the second enclosure around stator 804 that pass through the enclosure thereby maintaining the hermetic seal.

As depicted, recess 808 is on the top side of armature 804 for illustrative purposes only to show an example of where recess 808 may be located. In some embodiments, recess 808 is located on the bottom side of armature 804 with the top side of armature 804 being flat. Recess 808 may receive a plunger so that the plunger is seated within recess 808. Seating the plunger in recess 808 may prevent the plunger from moving, or sliding, when armature 804 moves. In some embodiments, recess 808 may be a hole through armature 806 and a spring (not shown) may be attached to the top of armature 806 (e.g., similar to spring 416 described above). When armature 806 moves toward stator 804 the spring may push the plunger instead of armature 806.

When a voltage is applied to motor coil 802 a magnetic field is generated in stator 804. The magnetic field generated in stator 804 attracts armature 806 toward stator 806 causing armature 806 to move. The motor coil 802 surrounding stator 804 and powered by a power source, such as a battery or capacitor, forms an electromagnet. Furthermore, motor coil 802, stator 804, and armature 806 may be considered to be an electric motor. Because recess 808 is located near the second end 806B, tension from the plunger in recess 808 creates an off-center load on armature 806. Because of off-center load caused by the plunger, first side 806A may be closer to stator 804 than second side 806B. For example, first side 806A may contact stator 804 before second side 806B causing a rotational force to be applied to armature 806 that axially translates the plunger. The plunger may be configured as plunger 216 in FIG. 2 to actuate a diaphragm as it moves axially, such as diaphragm 218, as described with respect to FIG. 2. The device 800 may further include additional components for forming a complete, implantable pump as described with respect to FIGS. 2 and 4.

Device 800 includes an efficient motor that may include improvements over current motors in at least one of size, power usage, and/or fabrication complexity. Device 800 is simple to fabricate requiring few components, specifically a single-piece stator, ferromagnetic material magnetically coupled to the stator, an armature, and a basic enclosure to surround the armature. No bonding or crimping is necessary and there are no air gaps in the stator. Additionally, a hermetically sealed, or impervious, enclosure may be placed around the coil of wires to protect them from any surrounding fluids as would be understood from the systems and devices described previously, such as the micropump 200 in FIG. 2.

Turning to FIGS. 9A-9D, illustrated are top and side views of a flat spring 900. Flat spring 900, also referred to as spring, may be an example of spring 416 described above with respect to motor 400 of FIG. 4. Spring 900 may be made of steel or titanium. Spring 900 may be made from a single sheet of metal or alloy. In at least one embodiment, spring 900 is made from a full hard 50 μm sheet of titanium. Spring 900 is designed as two serpentine springs joined together with one spring rotated 180° before joining. The bending of the spring provides the tension sufficient to move a plunger. Spring 900 can lay flat because of its camber. The camber of spring 900 provides a flatness tolerance of about 100 μm. This design and shape allows spring 900 to provide sufficient force to operate a pump, such as by pushing a plunger as described above. Spring 900 may perform over 300 million operations with little to no fatigue over a ten-year period.

Figures 9A, 9B, 9C, 9D:
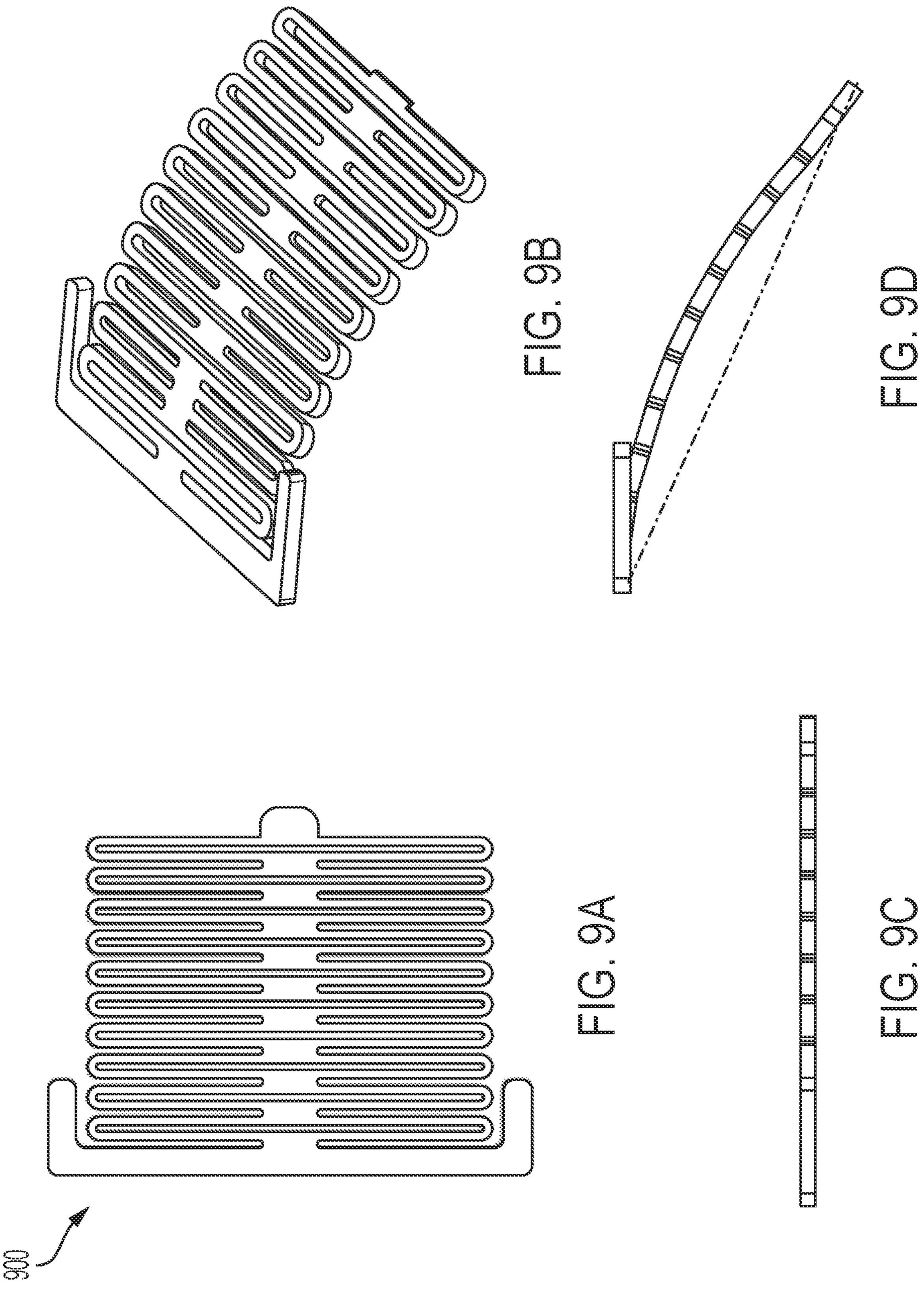
FIGS. 9A-9D are top down and side views of a spring for use in a motor of an implantable micropump motor, according to various aspects of the present disclosure.

As depicted in FIGS. 9A and 9C, spring 900 is flat and under tension, or preloaded, with energy stored to move a plunger. This is the state of spring 900 in the description above of FIG. 6A. When the armature is moved, as depicted in FIG. 6B, spring 900 exerts a force to return to the preloaded state, thereby moving the plunger. The preload force of spring 900 may be about 4 mN with a working stroke of about 80 μm.

Figures 10A, 10B:
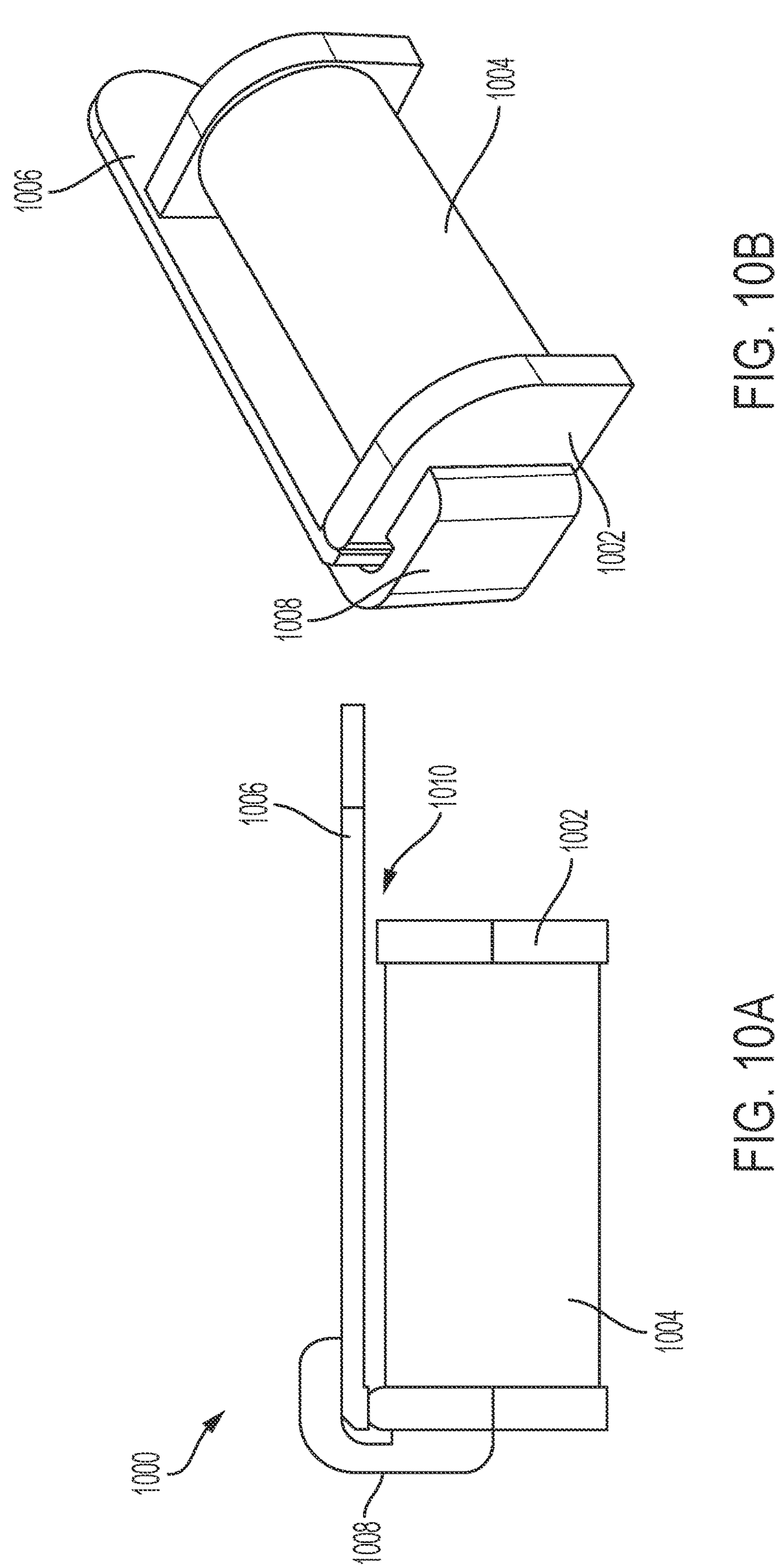

FIGS. 10A-10B depict motor 1000 according to at least one embodiment of the present disclosure. Motor 1000 includes a motor core 1002, a motor coil 1004, an armature 1006, and a hinge 1008. Motor coil 1004 may be a conductive material that is wrapped around motor core 1002. Armature 1006 may be attached to motor core 1002 by hinge 1008. The material used in motor coil 1004 may be wire having a diameter of about 10 μm. Motor coil 1004 may have between about 5,000 and about 15,000 turns around motor core 1002. There is an air gap 1010 between motor core 1002 and armature 1006. The air gap 1010 may be between about 85 μm and about 100 μm. When a voltage is applied to motor coil 1004 a magnetic field is generated that attracts armature 1006 toward the motor core 1002. The resulting movement of armature 1006 generates a torque and applies a force to an end of armature 1006 opposite hinge 1008. A plunger may be attached to the end of armature 1006 so that the plunger actuates a diaphragm when the armature 1006 moves.

Varying the number of turns on motor coil 1004 and the size of air gap 1010 may vary the power draw and vary the torque and force provided. Motor 1000 may draw between about 5.2 milliwatts (mW) and about 13.2 mW of power to produce between about 36.9 micronewton meters (μNm) and about 76.2 μNm of torque and between about 11 mN and about 42 mN of force by armature 1006. For example, when motor coil 1004 has 15,000 turns and air gap 1010 is about 100 μm motor 1000 draws about 13 mW of power and generates about 27 μNm of torque and about 11.7 mN of force by arm 1006. In another example, when motor coil 1004 has 6,000 turns and air gap 1010 is about 85 μm motor 1000 draws about 5.3 mW of power and produces about 76.2 μm of torque and about 41.3 mN force at armature 1006.

Figures 11A, 11B:
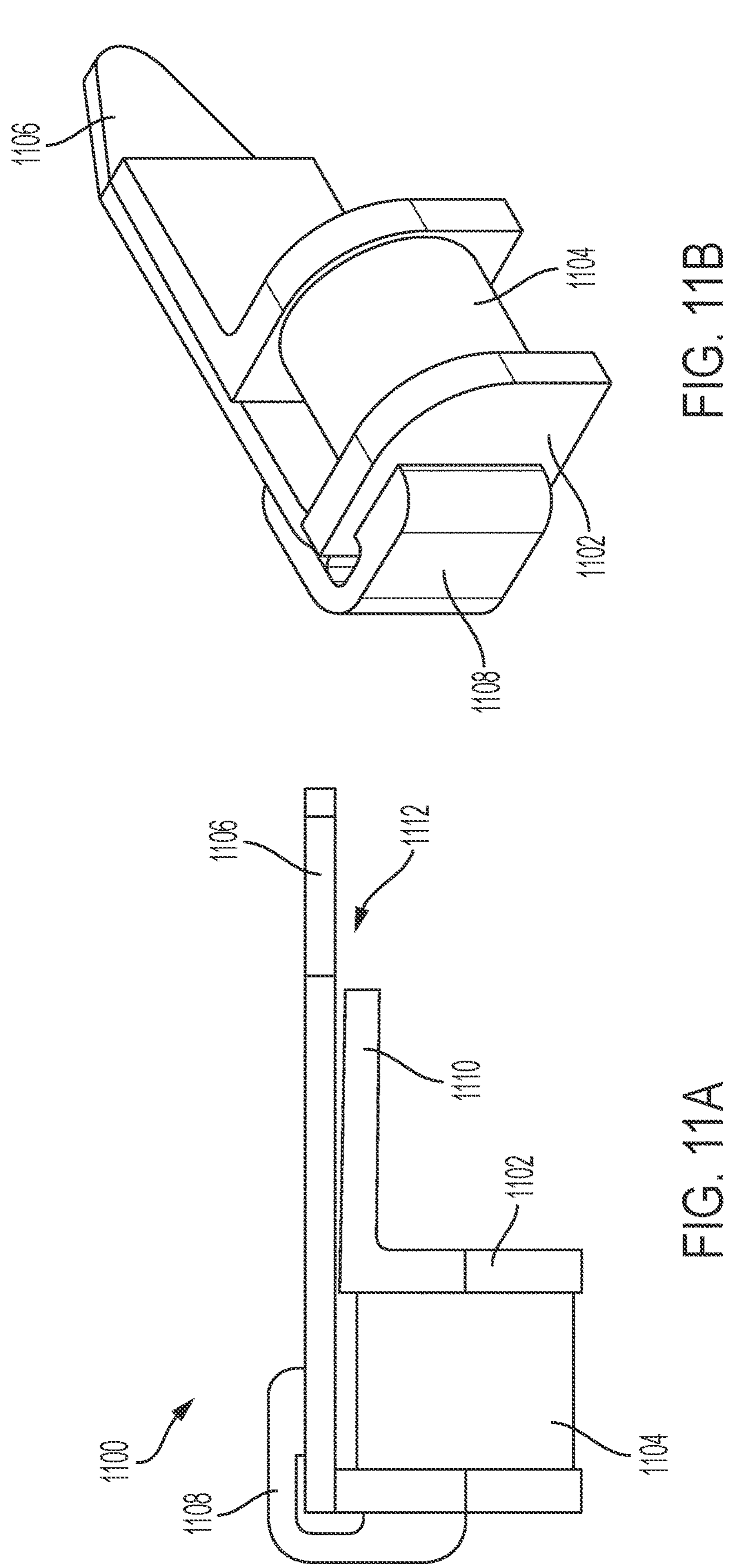

FIGS. 11A-11B depict a motor 1100 according to at least one embodiment of the present disclosure. Motor 1100 includes a motor core 1102, a motor coil 1104, an armature 1106, a hinge 1108, and a stator arm 1110. Armature 1106 is attached to motor core 1102 by hinge 1108. Stator arm 1110 extends perpendicular to a sidewall of motor core 1102 and approximately parallel to armature 1106. In some embodiments, stator arm 1110 may be between about 0.1 mm and about 2 mm shorter than armature 1106. In some embodiments, motor coil 1104 may include wire having a diameter of about 10 μm. Motor coil 1004 may have between about 5,000 and about 15,000 turns around motor core 1002. An air gap 1112 may be between motor core 1102 and armature 1106. Air gap 1112 may be between about 85 μm and about 100 μm. When a voltage is applied to motor coil 1104, a magnetic field is generated in stator arm 1110 that attracts armature 1106 thereby generating a torque and applying a force to an end of armature 1106 that is opposite hinge 1108. A plunger may be connected to the end of the armature 1106 to actuate a diaphragm. The force applied by armature 1106 may be sufficient to actuate the diaphragm to move fluid when motor 1100 is immersed.

Varying the number of turns on motor coil 1004 and the size of air gap 1112 may vary the power draw and vary the torque and force provided by motor 1100. Motor 1100 may draw between about 5.3 mW and about 13.2 mW of power to produce between about 36 μNm and about 75 μNm of torque and between about 11.7 mN and about 41.3 mN of force at armature 1006. For example, when motor coil 1104 has 6,000 turns and air gap 1112 is about 85 μm, motor 1100 draws about 5.3 mW of power and generates about 74.3 μNm of torque and about 40.4 mN of force at armature 1006.

When the current in motor coil 1104 drops to zero, a remnant flux may remain in the ferromagnetic material of the stator (e.g., core 1004, stator arm 1110) and armature 1106. Thus, motor 1100 may retain over 60% of its torque. The motor coil 1104 may be demagnetized by passing reverse current through the motor coil 1104. Three methods may be used to generate the reverse current. First, use a battery power and reverse current direction with a H-Bridge. Second, use a capacitor to oscillate current passively. Third, use a capacitor and a microcontroller to reverse the current. Options two and three use the magnetic energy stored in coil 1104 to provide the necessary power and therefore do not use any battery power.

Motor 1100 is a novel design for miniature motors in part because it is simple in design, including few parts, and is suitable for micromachining. Additionally, motor 1100 is directly powered by a battery that directly drives the load. This results in no energy being lost in electrical or mechanical conversions which improves the efficiency of the design. As discussed above, motor 1100 can be made flat and with a small footprint while still providing necessary force for various applications. Furthermore, experimentation and analysis have shown that the converging gap design of motor 1100 is at least two times more efficient than other magnetic actuator designs. Additionally, motor 1100 being a converging air gap style actuator produces 100% more torque than a comparably sized radial air gap actuator or a parallel air gap actuator.

Figure 12:
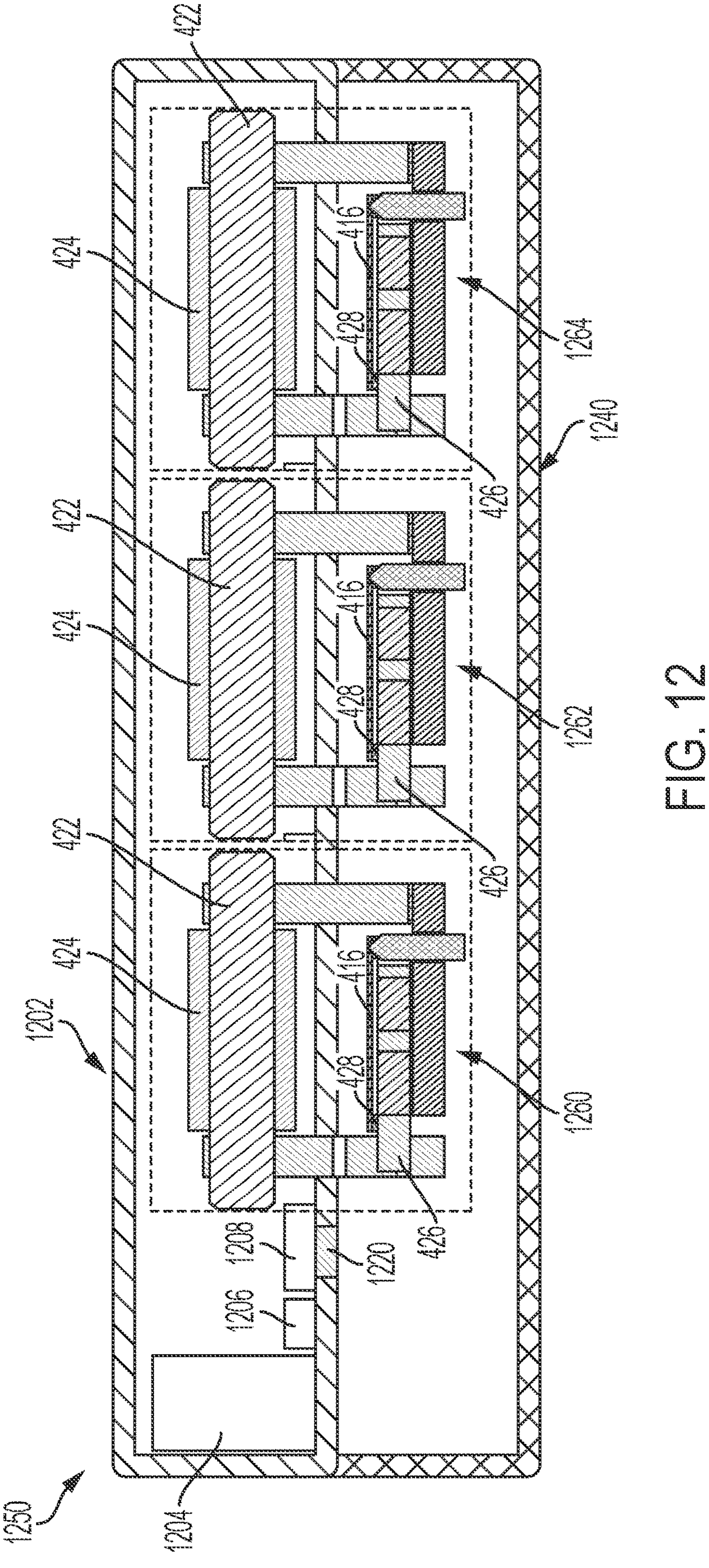
FIG. 12 is a cross section of another exemplary motor assembly for use in an implantable micropump, according to various aspects of the present disclosure.

FIG. 12 is a cross section of another exemplary motor assembly 1250 for use in an implantable micropump, according to various aspects of the present disclosure. Motor assembly 1250 may be coupled to a pump body and be configured to actuate pump body such as by moving, or displacing, various plungers. Motor assembly 1250 includes an enclosure 1202 including a power source 1204 (e.g., battery or capacitor), an IC 1206, a sensor 1208, and three electric motors 1260, 1262, and 1264 as shown. Each electric motor may be identical to the electric motor 400 described with respect to FIG. 4 (having identical components, some of which are labeled using the numbering of FIG. 4). For example, each of electric motors 1260, 1262, and 1264 includes a motor core 422, a motor coil 424, and a first portion of a stator, all located inside of enclosure 1202. Outside of enclosure 1202, each of motors 1260, 1262, and 1264 further includes a second portion of a stator, an armature, a spring 416, and a plunger. Motor assembly 1250 may also optionally include an enclosure 1240 that at least partially encloses the components outside of enclosure 402 as shown.

Motor assembly 1250 may be implanted and/or immersed in fluids. As with enclosure 402 of FIG. 4, enclosure 1202 is an air and/or gas filled enclosure that is hermetically sealed, or impervious, to ensure that no fluids enter enclosure 1202. Outside of enclosure 1202 is a fluid filled environment. The stator of each motor 1260, 1262, and 1264 extends from inside enclosure 1202 through walls of enclosure 1202 to outside of enclosure 1202. The electronic components of motor assembly 1250 (e.g., power source 1204, IC 1206, sensor 1208, and the motor core and motor coil of each motor 1260, 1262, and 1264) are placed inside of enclosure 1202 and are protected from the fluid outside of the enclosure 1202. In some embodiments, enclosure 1202 may be filled with a plastic, further protecting the electronic components inside.

As with FIG. 4, IC 1206 may be a microcontroller or an ASIC or other sort of processor. IC 406 may control the motor coil in motor 1260, the motor coil in motor 1262, and the motor coil in motor 1264. Sensor 1208 may be a pressure sensor that detects the pressure of the fluid surrounding enclosure 1202 through an opening 1220 in enclosure 1202. IC 1206 may receive pressure readings from sensor 1208 and control motor coils accordingly. In some examples, that may mean operating the motors 1260, 1262, and 1264 at a higher frequency when the sensor 1208 reads a high pressure. In some other examples, that may mean operating motors at a lower frequency when the sensor 1208 reads a high pressure. In either example, IC 1206 controls motor coils, and motors 1260, 1262, and 1264 by extension, in response to readings from sensor 1208. In some embodiments, motor assembly 1250 does not have a sensor 1208 and IC 1206 controls motor coils according to a pre-programmed cycle.

Figure 13:
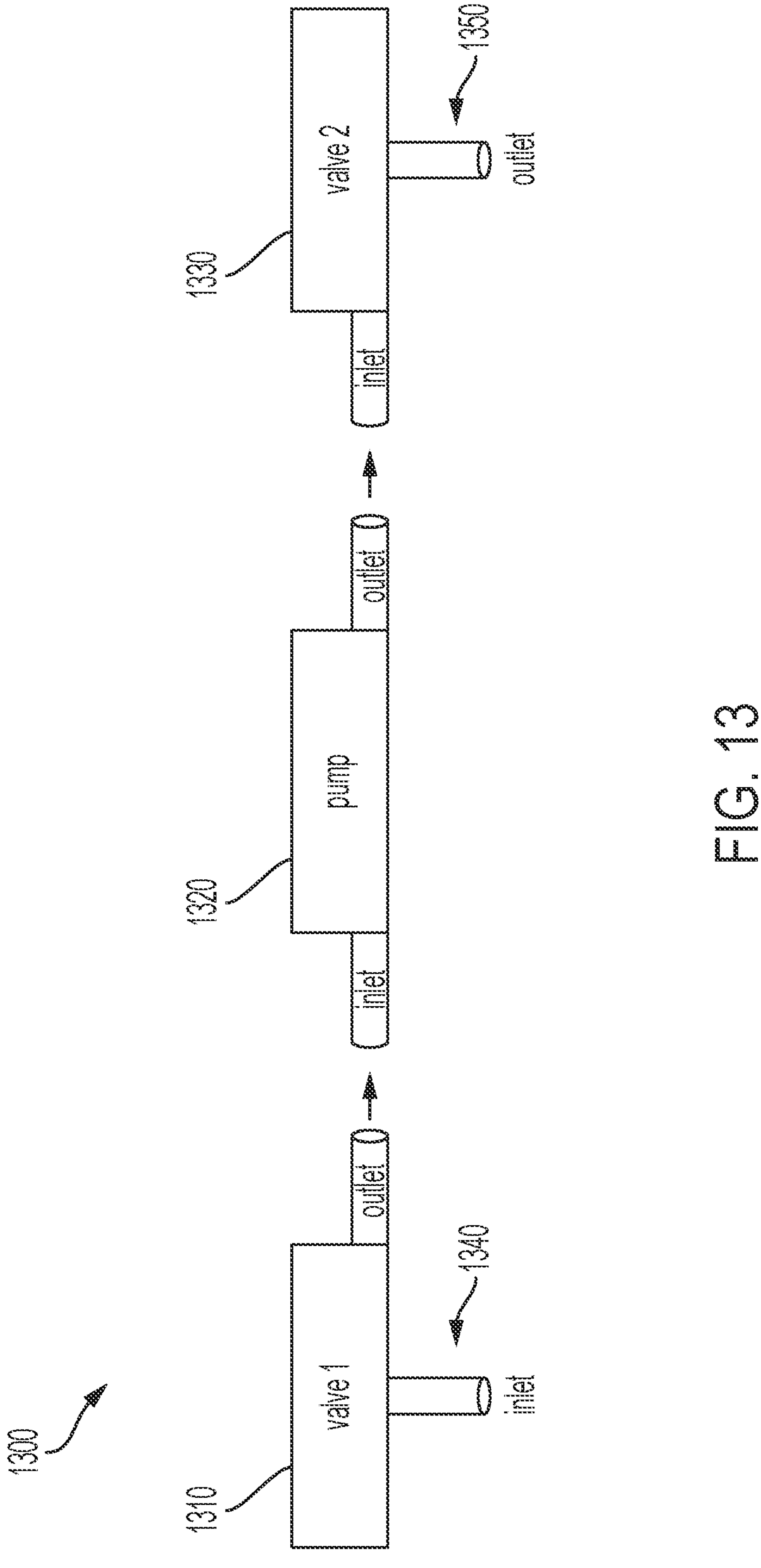
FIG. 13 is a functional diagram of an exemplary pump assembly, according to various aspects of the present disclosure.

FIG. 13 is a functional diagram of an exemplary pump body 1300, according to various aspects of the present disclosure. The pump assembly includes an inlet valve 1310, a pump chamber 1320 (also referred to as a compression chamber), an outlet valve 1330, an inlet 1340, and an outlet 1350. Each of the valves 1310 and 1330 as well as pump chamber 1320 may be mechanically actuated in various sequences to effect fluid moving from inlet 1340 to outlet 1350. In some embodiments, a device implantable in the human eye includes the motor assembly 1250 and the pump body 1300, with the motor assembly configured to actuate the inlet valve 1310, pump chamber 1320, and outlet valve 1330. For example, the inlet 1340 may be configured for receiving aqueous humor from the eye, and the outlet 1350 may be configured to discharge aqueous humor. In some embodiments, the outlet 1350 is in fluid communication with an exterior surface of the eye so that aqueous humor is drained outside of the eye (e.g., onto the exterior surface).

FIGS. 16 and 17 are tables of exemplary pump sequences that apply to micropumps or pump assemblies such as pump assembly 1300, according to various aspects of the present disclosure. A logic “0” in a table entry means the corresponding valve chamber is open to fluid flow and the pump chamber (labeled as “pump” in the table) is actively pressurized, and a logic “1” in a table entry represents that the corresponding valve chamber is closed to fluid flow and the pump chamber is not actively pressurized. An actively pressurized pump chamber may be the result of a membrane being fully or partially deformed by a plunger, such as that described with respect to FIG. 2. The pump sequence in FIG. 16 is a less efficient, but shorter pump sequence, than the pump sequence in FIG. 17. Referring to pump assembly 1300, step 1 in FIG. 16 represents a logic state in which the inlet valve 1310 and pump chamber 1320 are open (logic “0”) but the outlet valve 1330 is closed, thereby resulting in no fluid flowing from outlet 1350. From that step, proceeding to step 2, the inlet valve 1310 is closed. Proceeding next to step 3, the outlet valve 1330 is opened (logic “0”) and the pump chamber 1320 is pressurized, implying that a pump membrane has been deformed to force fluid out the outlet valve 1350, as the fluid is blocked from flowing through closed inlet valve 1340 in step 3. In each table in FIGS. 16 and 17, “Y” stands for “yes,” and “N” stands for “no.” As indicated in the table of FIG. 16, there is outlet flow (“Y”) but no inlet flow (“N”) in step 3. Next in step 4, the outlet valve 1330 is closed and the inlet valve 1310 is opened as compared to step 3. Next in step 5, the pump chamber 1320 is opened by removing pressure on the pump membrane. This results in fluid filling the pump chamber 1320 for the next sequence, which starts again in step 1. Switching between an open state and a closed state for a valve represents selectively unblocking (open state) and blocking (closed state) a valve to fluid flow. Similarly, switching between an open state and a closed state for a pump chamber represents selectively de-pressurizing (open state) and pressurizing (closed state) the pump chamber to fluid flow.

In FIG. 17, there are seven steps that are performed in a repeating pattern starting with step 1, proceeding to step 7, and then starting over again at step 1. The illustrated logic states represent the same thing as in FIG. 16 (i.e., logic “0” means open for the valve and unpressurized for the pump and logic “1” means closed for the valve and pressurized for the pump).

Figure 14:
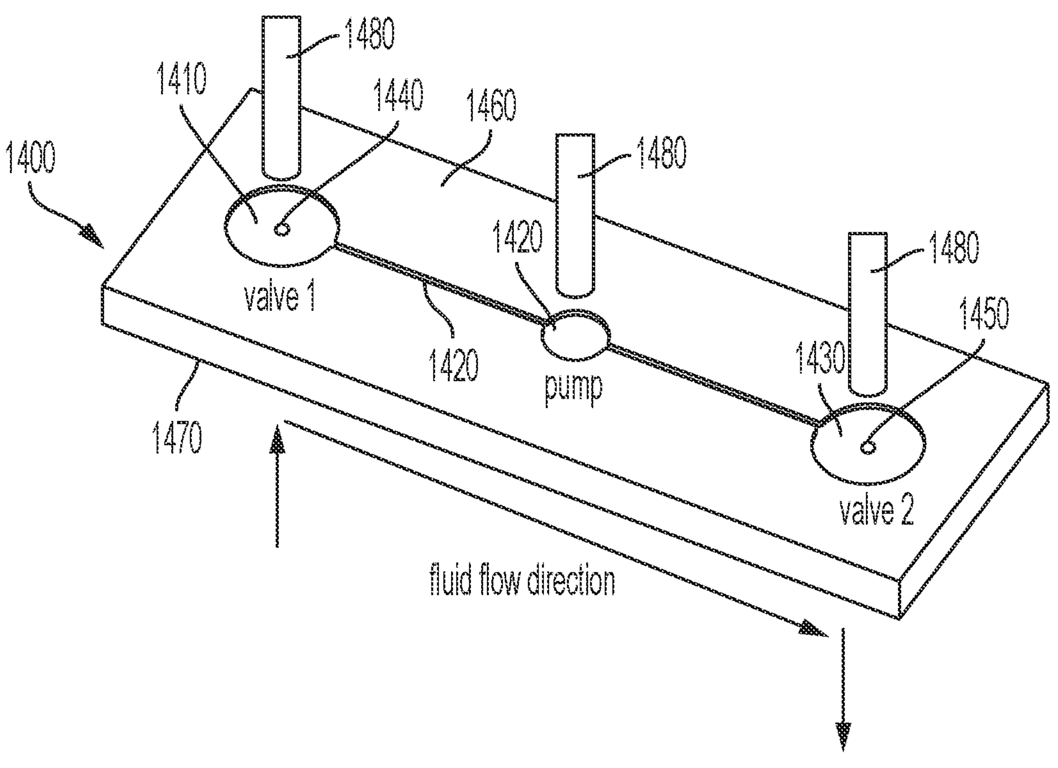
FIG. 14 is a perspective view of an exemplary pump structure, according to various aspects of the present disclosure.

FIG. 14 is a perspective view of an exemplary pump body 1400, according to various aspects of the present disclosure. Not shown is a flexible membrane that would cover the top side 1460 of pump body 1400. The pump body 1400 includes a solid material layer having portions removed to form an inlet valve chamber 1410, a pump chamber 1420 (also referred to as a compression chamber), and an outlet valve chamber 1430. There is a hole 1440 extending through pump body 1400 to form a channel to allow fluid to flow from bottom side 1470 through the pump body 1420 to the top side 1460. Pump body 1400 further includes a channel 1420 that connects valve chamber 1410 to pump chamber 1420 and pump chamber 1420 to valve chamber 1430. There is a hole 1450 in outlet valve chamber 1430, and the hole 1450 extends all the way through pump body 1400 to the bottom side 1470 to form a channel. This channel allows fluid to flow from the channel 1420 and out of the pump body 1420. Also shown are three plungers 1480 that are each part of a motor (not shown), such as motor 400 shown in FIG. 4. Each plunger 1480 may be a plunger, such as plunger 418 in FIG. 4, for example.

Each of the plungers 1480 may be operated to open or close inlet valve chamber 1410 and valve chamber 1430, or to pressurize and de-pressurize pump chamber 1420. For example, if the plunger 1480 above valve chamber 1410 is actuated downward to depress a pump diaphragm or membrane (not shown) so that hole 1440 is covered, then fluid cannot flow into valve chamber 1410.

Figure 15:
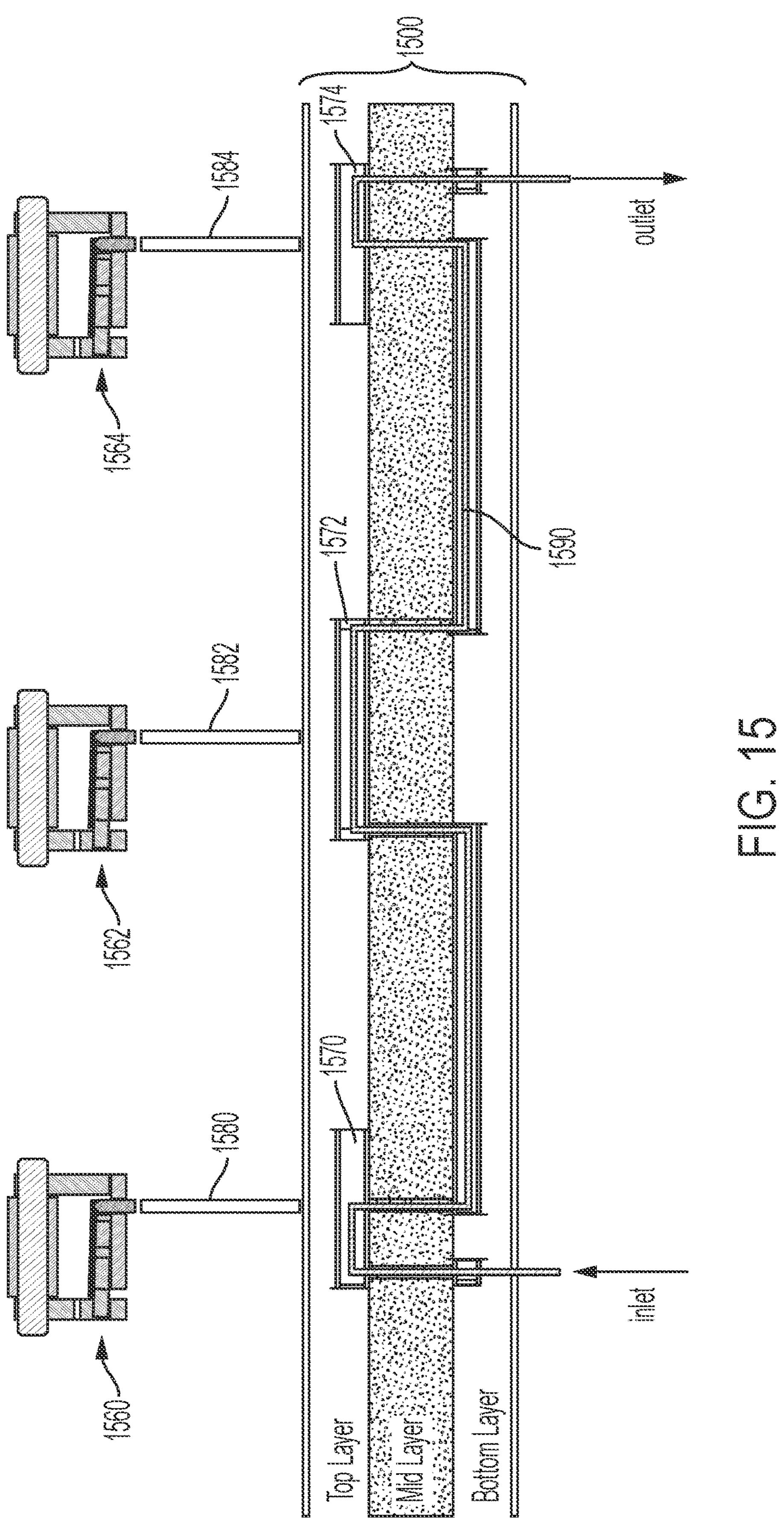
FIG. 15 is a cross-section of an exemplary pump structure positioned relative to motors, according to various aspects of the present disclosure.

FIG. 15 is a cross-section of an exemplary pump body 1500 positioned proximate to motors 1560, 1562, and 1564, according to various aspects of the present disclosure. The motors 1560, 1562, and 1564 may represent motors 1260, 1262, and 1264, respectively, in FIG. 12, for example, in which case motors 1560, 1562, and 1564 are shown with the other components of an associated motor assembly for illustration and convenience. In this embodiment, the pump body 1500 includes three layers: a top layer, a middle layer, and a bottom layer as shown. The top layer may be a flexible membrane (or diaphragm), and the middle layer may be a non-flexible or hard material, such as a plastic. The bottom layer can be made of the same material as either the middle layer or top layer. The pump body 1500 includes an inlet valve chamber 1570, a compression chamber 1572, and an outlet valve chamber 1574.

Motor 1560 includes or is coupled to a plunger 1580; motor 1562 includes or is coupled to a plunger 1582; and motor 1564 includes or is coupled to a plunger 1584. Actuation of each plunger in an axial direction depresses the top layer into respective chambers 1570, 1572 and 1574 and acts to block fluid flow in the case of chambers 1570 and 1574 and acts to pressurize chamber in the case of chamber 1572. The direction of fluid flow into and through inlet chamber 1570, through the pump body 1500 and into compression chamber 1572, and further through pump body 1500 into outlet valve 1574 and out of the pump body 1574 is indicated in FIG. 15 as 1590.

The motors 1560, 1562, and 1564 can operate according to the tables of exemplary pump sequences in FIGS. 16 and 17. Logic "1" in the tables represents axial extension of the respective plunger into a chamber to close the chamber, and logic "0" in the tables represents the top layer of pump body 1500 being flat with the respective chamber being open. Plunger 1580 controls the action of inlet chamber 1570, plunger 1582 controls the action in compression (or pump) chamber 1572, and plunger 1584 controls the action of outlet valve chamber 1574, as represented by the logic state in the tables. Motor 1560 controls plunger 1580 to selectively block and unblock inlet valve chamber 1570 to fluid flow. Likewise, motor 1562 controls plunger 1582 to selectively block and unblock the compression chamber to fluid flow. Likewise, motor 1564 controls plunger 1584 to selectively block and unblock outlet valve chamber 1574 to fluid flow.

Although the embodiments of the present disclosure are described with respect to regulating IOP (e.g., for glaucoma patients), it will be understood that the devices, systems, and methods described herein may be used to treat other ophthalmic conditions instead of or in addition to high IOP. For example, because the devices described herein can drain AH into the tear film, the devices described herein may be configured for treating dry eye conditions.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A micropump implantable in an eye, comprising:

a ferromagnetic member;

a power source;

a motor coil magnetically coupled to the ferromagnetic member and electrically coupled to the power source to receive power from the power source, wherein the motor coil is configured to generate a magnetic field in the ferromagnetic member when power is applied to the motor coil by the power source;

a housing enclosing the motor coil and the power source and partially enclosing the ferromagnetic member, wherein the housing is hermetically sealed;

a pump diaphragm;

a compression chamber at least partially defined by the pump diaphragm and having an inlet and an outlet;

an armature configured to move in response to the magnetic field in the ferromagnetic member; and wherein the pump diaphragm is configured to cause fluid to flow through the compression chamber from the inlet to the outlet in response to movement of the armature, and wherein the pump diaphragm, the compression chamber, the armature, and a portion of the ferromagnetic member are located outside of the housing.

2. The micropump of claim 1, wherein the portion of the ferromagnetic member defines part of an expansion chamber, and wherein the expansion chamber encloses the spring and the armature.

3. The micropump of claim 1, further comprising:

an opening in the ferromagnetic member through which fluid may flow into the expansion chamber responsive to actuation of the pump diaphragm.

4. The micropump of claim 1, further comprising a spring having a first end and a second end opposite the first end, wherein the armature comprises a first side and a second side opposing the first side, wherein the first end is connected to the housing and the second end is connected to the first side of the armature, and wherein the second side of the armature is configured to drive the pump diaphragm.

5. The micropump of claim 4, wherein the pump further includes:

a first one-way valve that prevents fluid from flowing from the outlet to the chamber; and a second one-way valve that prevents fluid from flowing from the chamber to the inlet.

6. The micropump of claim 1, wherein the power source is a battery or a capacitor.

7. The micropump of claim 1, wherein the ferromagnetic member extends through the housing such that the portion of the ferromagnetic member is located outside of the housing.

8. The micropump of claim 1, further comprising:

an inlet valve chamber in fluid communication with the compression chamber, wherein the inlet valve chamber is at least partially defined by the pump diaphragm;

an outlet valve chamber in fluid communication with the compression chamber, wherein the inlet valve chamber is at least partially defined by the pump diaphragm;

a plunger;

a second plunger; and a third plunger, wherein the plunger is configured to actuate the pump diaphragm to selectively block and unblock the compression chamber, the second plunger is configured to actuate the pump diaphragm to selectively block and unblock the inlet valve chamber, and the third plunger is configured to configured to actuate the pump diaphragm to selectively block and unblock the outlet valve chamber to effectuate fluid flow into the inlet valve chamber through the compression chamber and out of the outlet valve chamber.

9. An implantable micropump, comprising:

a ferromagnetic core;

a coil comprising multiple windings around the ferromagnetic core;

a ferromagnetic member connected to the ferromagnetic core;

a power source coupled to the coil and configured to provide power to the coil, wherein the coil is configured to generate a magnetic field in the ferromagnetic core and the ferromagnetic member in response to the power source providing power to the coil;

a housing enclosing the coil and the power source and partially enclosing the ferromagnetic member, wherein the housing is impervious, and wherein a portion of the ferromagnetic member extends through the housing; and an armature configured to move in response to the magnetic field in the ferromagnetic member and configured to cause fluid to flow through the implantable micropump.

10. The implantable micropump of claim 9, further comprising:

a plunger, wherein the armature includes an opening through which the plunger passes; and a spring coupled to the armature and configured to axially translate the plunger through the opening in the armature in response to rotation of the armature.

11. The implantable micropump of claim 10, further comprising:

a diaphragm, wherein the plunger is configured to actuate the diaphragm causing the diaphragm to move fluid.

12. The implantable micropump of claim 9, further comprising:

an integrated circuit configured to control the power provided by the power source to the coil.

13. The implantable micropump of claim 9, further comprising:

an integrated circuit that controls the power to the coil; and a pressure sensor that sends pressure readings to the integrated circuit, wherein the integrated determines when to power the coil based on the pressure readings.

14. The implantable micropump of claim 9, wherein the armature includes at least one slot.

15. The implantable micropump of claim 9, wherein ferromagnetic core is a first ferromagnetic core and the coil is a first coil, and wherein the implantable micropump further includes:

a second ferromagnetic core; and a second coil, including multiple windings around the second ferromagnetic core, wherein the second ferromagnetic core is connected to the ferromagnetic member.

* * * * *